United States Patent
Yang et al.

(10) Patent No.: US 9,796,720 B2
(45) Date of Patent: Oct. 24, 2017

(54) IMIDAZOLE-DERIVED MODULATORS OF THE GLUCOCORTICOID RECEPTOR

(71) Applicant: BRISTOL-MYERS SQUIBB COMPANY, Princeton, NJ (US)

(72) Inventors: Michael G. Yang, Narbeth, PA (US); Zili Xiao, East Windsor, NJ (US); David S. Weinstein, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/911,476

(22) PCT Filed: Aug. 21, 2014

(86) PCT No.: PCT/US2014/052006
§ 371 (c)(1),
(2) Date: Feb. 11, 2016

(87) PCT Pub. No.: WO2015/027015
PCT Pub. Date: Feb. 26, 2015

(65) Prior Publication Data
US 2016/0200728 A1  Jul. 14, 2016

Related U.S. Application Data

(60) Provisional application No. 61/868,651, filed on Aug. 22, 2013.

(51) Int. Cl.
*C07D 413/06* (2006.01)
*C07D 413/14* (2006.01)
*C07D 487/04* (2006.01)

(52) U.S. Cl.
CPC ......... *C07D 487/04* (2013.01); *C07D 413/06* (2013.01); *C07D 413/14* (2013.01)

(58) Field of Classification Search
CPC .............................. C07D 413/06; C07D 413/14
See application file for complete search history.

(56) References Cited

U.S. PATENT DOCUMENTS

| 2,746,992 | A | 5/1956 | Goldberg et al. |
| 5,478,853 | A | 12/1995 | Regnier et al. |
| 5,506,245 | A | 4/1996 | Regnier et al. |
| 5,594,001 | A | 1/1997 | Teleha et al. |
| 5,750,528 | A | 5/1998 | Brown et al. |
| 7,056,911 | B1 * | 6/2006 | Rosowsky ........... C07D 239/48 514/217 |
| 8,034,940 | B2 | 10/2011 | Weinstein et al. |

FOREIGN PATENT DOCUMENTS

| AT | 186643 B | 8/1956 |
| WO | WO94/24131 A1 | 10/1994 |
| WO | WO99/00535 A1 | 1/1999 |
| WO | WO01/09137 A1 | 2/2001 |
| WO | WO2004/054504 A2 | 7/2004 |
| WO | WO2007/085558 A1 | 8/2007 |
| WO | WO2008/021926 A2 | 2/2008 |
| WO | WO2009/108525 A2 | 9/2009 |
| WO | WO2011/115928 A1 | 9/2011 |
| WO | WO2013/044092 A1 | 3/2013 |

OTHER PUBLICATIONS

Takahashi et al. (Bioorg. Med. Chem. Lett. 17 (2007) 5091-5095).*
Thompson et al. (Bioorg. Med. Chem. Lett. 17 (2007) 3354-3361).*
Kubinyi (3D QSAR in Drug Design: Ligand-Protein Interactions and Molecular Similarity, vol. 2-3, Springer, 1998, 800 pages). pp. 243-244 provied.*
Wermuth, The Practice of Medicinal Chemsitry, 2d ed. (2003), 768 pages, Chs. 9-10 provided.*
CAS Registry No. 1350027-85-8, Entered STN: Dec. 7, 2011.
CAS Registry No. 1349707-09-0, Entered STN: Dec. 6, 2011.
CAS Registry No. 1349534-78-6, Entered STN: Dec. 6, 2011.
CAS Registry No. 1349465-96-8, Entered STN: Dec. 6, 2011.
CAS Registry No. 1349150-45-3, Entered STN: Dec. 5, 2011.
CAS Registry No. 1348306-04-6, Entered STN: Dec. 4, 2011.
CAS Registry No. 1348033-49-7, Entered STN: Dec. 4, 2011.
CAS Registry No. 1347914-89-9, Entered STN: Dec. 4, 2011.
CAS Registry No. 1347835-92-0, Entered STN: Dec. 4, 2011.
CAS Registry No. 1347721-70-3, Entered STN: Dec. 2, 2011.
CAS Registry No. 1347521-79-2, Entered STN: Dec. 2, 2011.
CAS Registry No. 1008119-40-1, Entered STN: Mar. 16, 2008.
CAS Registry No. 1008119-36-5, Entered STN: Mar. 16, 2008.
CAS Registry No. 1008119-34-3, Entered STN: Mar. 16, 2008.

(Continued)

*Primary Examiner* — Robert Havlin
(74) *Attorney, Agent, or Firm* — Hong Liu

(57) ABSTRACT

Novel non-steroidal compounds are provided which are useful in treating diseases or disorders associated with modulation of the glucocorticoid receptor, AP-1, and/or NF-κB activity, including metabolic and inflammatory and immune diseases or disorders, having the structure of formula (I): an enantiomer, diastereomer, or tautomer thereof, or a prodrug ester thereof, or a pharmaceutically-acceptable salt thereof, in which the variables are as defined in the specification.

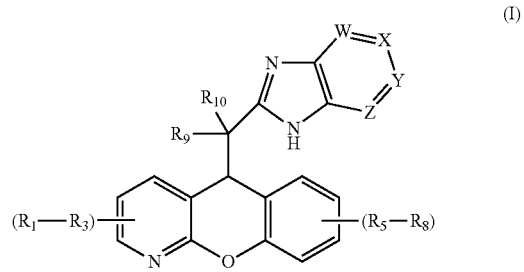

10 Claims, No Drawings

(56) References Cited

OTHER PUBLICATIONS

CAS Registry No. 1008119-32-1, Entered STN: Mar. 16, 2008.
CAS Registry No. 1008119-27-4, Entered STN: Mar. 16, 2008.
CAS Registry No. 1008118-50-0, Entered STN: Mar. 16, 2008.
CAS Registry No. 1008117-95-0, Entered STN: Mar. 16, 2008.
CAS Registry No. 1008117-93-8, Entered STN: Mar. 16, 2008.
CAS Registry No. 1008117-90-5, Entered STN: Mar. 16, 2008.
CAS Registry No. 1008117-79-0, Entered STN: Mar. 16, 2008.
CAS Registry No. 1008117-77-8, Entered STN: Mar. 16, 2008.
CAS Registry No. 1008117-64-3, Entered STN: Mar. 16, 2008.
CAS Registry No. 1008117-62-1, Entered STN: Mar. 16, 2008.
CAS Registry No. 1008117-54-1, Entered STN: Mar. 16, 2008.
CAS Registry No. 1008117-52-9, Entered STN: Mar. 14, 2008.
CAS Registry No. 1008117-50-7, Entered STN: Mar. 14, 2008.
CAS Registry No. 1008117-47-2, Entered STN: Mar. 14, 2008.
CAS Registry No. 1008117-44-9, Entered STN: Mar. 14, 2008.
CAS Registry No. 1008117-41-6, Entered STN: Mar. 14, 2008.
CAS Registry No. 1008117-39-2, Entered STN: Mar. 14, 2008.
CAS Registry No. 1008117-37-0, Entered STN: Mar. 14, 2008.
CAS Registry No. 1008117-35-8, Entered STN: Mar. 14, 2008.
CAS Registry No. 1008117-33-6, Entered STN: Mar. 14, 2008.
Evdokimoff et al., "9-Substituted xanthene derivatives, III", Annali di Chimica (Rome, Italy) vol. 57(12), pp. 1520-1532 (1967).
Gong, Hua et al., "Discovery of acylurea isosteres of 2-acylaminothiadiazole in the azaxanthene series of glucocorticoid receptor agonists", Bioorganic & Medicinal Chemistry Letters, vol. 24, pp. 3268-3273 (2014).
Villani, Frank et al., "Benzopyranopyridine Derivatives.1. Aminoalkyl Derivatives of the Azaxanthenes as ironchodilating Agents", Journal of Medicinal Chemistry, vol. 18(1), pp. 1-8 (1975).
Weinstein, David et al., Azaxanthene Based Selective Glucocorticoid Receptor Modulators: Design, Synthesis, and Pharmacological Evaluation of (S)-4(5-(1-((1,3,4-Thiadiazol-2-yl)amino)-2-methyl-1-oxopropan-2-yl)-5H-chromeno[2,3-b]pyridine-2-yl)-2-fluoro-N,N-dimethylbenzamide (BMS-776532) and Its Methylene Homologue (BMS-791826), Journal of Medicinal Chemistry, vol. 54, pp. 7318-73333 (2011).

* cited by examiner

IMIDAZOLE-DERIVED MODULATORS OF THE GLUCOCORTICOID RECEPTOR

CROSS REFERENCE TO RELATED APPLICATIONS

This application is entitled to priority pursuant to 35 U.S.C. §119(e) to U.S. provisional patent application No. 61/868,651, filed on Aug. 22, 2013, which is incorporated herein in its entirety.

FIELD OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions thereof and methods for using such compounds and compositions to treat these and related diseases or disorders.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *J. Clin. Invest.*, 107:3 (2001); Firestein, G. S. et al., *Arthritis and Rheumatism*, 42:609 (1999); and Peltz, G., *Curr. Opin. Biotech.*, 8:467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease.

See Manning, A. M. et al., *Nature Rev. Drug Disc.*, 2:554 (2003).

A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke, J. R., *Curr. Opin. Drug Discov. Devel.*, 6(5):720-728 (September 2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228:740-742 (1985); Weinberger et al., *Nature*, 318:670-672 (1986) and for results in rats see Miesfeld, R., *Nature*, 312:779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62:1189 (1990); Yang-Yen, H. F. et al., *Cell*, 62:1205 (1990); Diamond, M. I. et al., *Science*, 249:1266 (1990); and Caldenhoven, E. et al., *Mol. Endocrinol.*, 9:401 (1995). Other mechanisms such as sequestration of co-activators by GR have also been proposed. See Kamei, Y. et al., *Cell*, 85:403 (1996); and Chakravarti, D. et al., *Nature*, 383:99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell*, 93:531 (1998) and Reichardt, H. M., *EMBO J.*, 20:7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions and combinations thereof and methods for using such compounds, combinations and compositions to treat these and related diseases or disorders.

In accordance with one aspect of the invention (Embodiment 1), compounds are provided having the structure of formula I

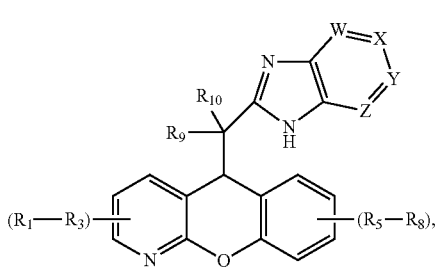

I an enantiomer, diastereomer, tautomer, or a pharmaceutically-acceptable salt thereof, wherein:

W, X, Y and Z are independently selected from N and $CR_4$;

$R_1$, $R_2$, $R_3$, $R_4$, $R_5$, $R_6$, $R_7$, and $R_8$ are the same or different and at each occurrence are independently selected from hydrogen, halogen, $C_{1-8}$alkyl, substituted $C_{1-8}$alkyl, $C_{2-8}$alkenyl, substituted $C_{2-8}$alkenyl, $C_{2-8}$alkynyl, $C_{2-8}$substituted alkynyl, nitro, cyano, $OR_{12}$, $-NR_{12}R_{13}$, $-C(=O)R_{12}$, $-C(=O)OR_{12}$, $-C(=O)NR_{12}R_{13}$, $-OC(=O)NR_{12}R_{13}$, $-NR_{12}C(=O)NR_{13}R_{14}$, $-OC(=O)R_{12}$, $-NR_{12}C(=O)R_{13}$, $-NR_{12}C(O)OR_{13}$, $-NR_{12}C(S)OR_{13}$, $S(O)_pR_{14}$, $NR_{12}SO_2R_{14}$, dialkylaminoalkoxy, alkoxyalkyloxyalkyloxy, $SO_2NR_{12}R_{13}$, $C_{3-7}$cycloalkyl, $C_{3-7}$cycloalkenyl, $C_{3-7}$cycloalkynyl, heterocyclo, aryl, and heteroaryl, wherein said cycloalkyl, cycloalkenyl, heterocyclo, aryl, and heteroaryl are each substituted with zero to three $R_{11}$;

$R_9$ and $R_{10}$ are the same or different and at each occurrence are independently $C_{1-6}$alkyl; or $R_9$ and $R_{10}$ are taken together with the atom to which they are attached to form a $C_{3-7}$cycloalkyl, $C_{3-7}$cycloalkenyl, or heterocyclo group;

$R_{11}$ at each occurrence is independently selected from halogen, $C_{1-6}$alkyl, $C_{1-6}$hydroxyalkyl, $C_{1-6}$haloalkyl, $C_{1-6}$alkoxy, $C_{1-6}$haloalkoxy, $-OR_{12}$, $=O$, $-NR_{12}R_{13}$, $-C(=O)R_{12}$, $-C(=O)OR_{12}$, $-C(=O)NR_{12}R_{13}$, $-OC(=O)NR_{12}R_{13}$, $-NR_{12}C(O)NR_{12}R_{13}$, $-OC(=O)R_{12}$, $-NR_{12}C(=O)R_{13}$, $-NR_{12}C(O)OR_{13}$, $-NR_{12}C(S)OR_{13}$, $-S(O)_pR_{14}$, $-NR_{12}SO_2R_{14}$, $SO_2NR_{12}R_{13}$, $C_{3-7}$cycloalkyl, 3- to 6-membered heterocyclo, phenyl, and 5- to 6-membered heteroaryl substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_{12}$ and $R_{13}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{12}$ is taken together with $R_{13}$ to form a heteroaryl or heterocyclo ring;

$R_{14}$ at each occurrence is independently selected from $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo;

p is 0, 1 and 2.

Other Embodiments of the present invention are as described below.

Embodiment 2: a compound as defined in Embodiment 1, or an enantiomer, diastereomer, tautomer, or a pharmaceutically-acceptable salt thereof, wherein:

$R_1$, $R_2$, and $R_3$ are the same or different and at each occurrence are independently selected from hydrogen, halogen, $C_{1-8}$alkyl, cyano, $C_{3-7}$cycloalkyl, 3- to 10-membered heterocyclo, 5- to 10-membered aryl, and 5- to 10-membered heteroaryl, wherein said alkyl, alkoxy, cycloalkyl, heterocyclo, aryl, and heteroaryl are each substituted with zero to three substituents independently selected from halogen, $C_{1-6}$alkyl, $C_{1-6}$hydroxyalkyl, $C_{1-6}$haloalkyl, $C_{1-6}$alkoxy, $C_{1-6}$haloalkoxy, $-OR_{12}$, $-NR_{12}R_{13}$, $-C(=O)R_{12}$, $-C(=O)OR_{12}$, $-C(=O)NR_{12}R_{13}$, $-OC(=O)NR_{12}R_{13}$, $-NR_{12}C(O)NR_{12}R_{13}$, $-OC(=O)R_{12}$, $-NR_{12}C(=O)R_{13}$, $-NR_{12}C(O)OR_{13}$, $-NR_{12}C(S)OR_{13}$, $-S(O)_pR_{14}$, $-NR_{12}SO_2R_{14}$, $SO_2NR_{12}R_{13}$, $C_{3-7}$cycloalkyl, 3- to 6-membered heterocyclo, phenyl, and 5- to 6-membered heteroaryl substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_4$ is selected from hydrogen and $C_{1-6}$alkyl;

$R_5$, $R_6$, $R_7$, and $R_8$ are the same or different and at each occurrence are independently selected from hydrogen, halogen, and $C_{1-6}$alkyl;

$R_{12}$ and $R_{13}$ are the same or different and at each occurrence are independently selected from (i) hydrogen, $C_{1-6}$alkyl, $C_{1-6}$hydroxyalkyl, $C_{1-6}$haloalkyl, $C_{1-6}$alkoxy, $C_{1-6}$haloalkoxy, $C_{3-7}$cycloalkyl, phenyl, 5- to 6-membered heteroaryl, and 5- to 6-membered heterocyclo; or (ii) where possible, $R_{12}$ is taken together with $R_{13}$ to form a 5- to 6-membered heteroaryl or 5- to 6-membered heterocyclo ring; and $R_{14}$ at each occurrence is independently selected from $C_{1-6}$alkyl, $C_{1-6}$hydroxyalkyl, $C_{1-6}$haloalkyl, $C_{1-6}$alkoxy, $C_{1-6}$haloalkoxy, $C_{3-7}$cycloalkyl, phenyl, 5- to 6-membered heteroaryl, and 5- to 6-membered heterocyclo.

Embodiment 3: a compound as defined in Embodiments 1-2, having the following formula II:

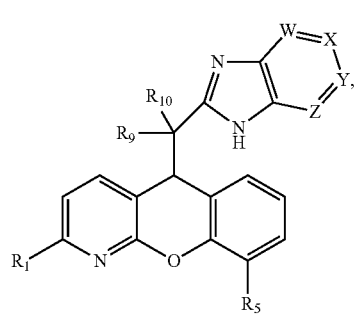

II or an enantiomer, diastereomer, tautomer, or a pharmaceutically-acceptable salt thereof, wherein:

W, X, Y and Z are independently selected from N and CH;

$R_1$ is selected from 5- to 10-membered aryl and 5- to 10-membered heteroaryl, wherein said aryl and heteroaryl group are each substituted with zero three substituents independently selected from halogen, $C_{1-6}$hydroxyalkyl, —OR$_{12}$, —NR$_{12}$R$_{13}$, —C(═O)R$_{12}$, —C(═O)OR$_{12}$, —C(═O)NR$_{12}$,R$_{13}$, —NR$_{12}$C(═O)R$_{13}$, —S(O)$_2$R$_{14}$, —NR$_{12}$SO$_2$R$_{14}$, and 5- to 6-membered heteroaryl substituted with C$_{1-3}$alkyl group.

R$_5$ is halogen;

R$_9$ and R$_{10}$ are the same or different and at each occurrence are independently C$_{1-3}$alkyl;

R$_{12}$ and R$_{13}$ are the same or different and at each occurrence are independently selected from (i) hydrogen, C$_{1-6}$alkyl, C$_{1-6}$haloalkyl, and 5- to 6-membered heterocyclo; or (ii) where possible, R$_{12}$ is taken together with R$_{13}$ to form a 5- to 6-membered heterocyclo ring; and R$_{14}$ at each occurrence is independently C$_{1-6}$alkyl.

Embodiment 4: a compound as defined in Embodiments 1-3, having the following formula III

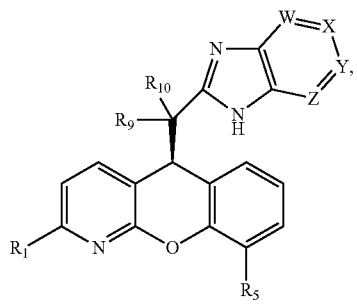

III or an enantiomer, diastereomer, tautomer, or a pharmaceutically-acceptable salt, thereof.

Embodiment 5: the compound as defined in Embodiments 1-4, or an enantiomer, diastereomer, tautomer, or a pharmaceutically-acceptable salt thereof, wherein:

R$_1$ is phenyl or pyridyl, each of which is substituted with zero to three substituents independently selected from halogen, C$_{1-6}$hydroxyalkyl, —OR$_{12}$, —NR$_{12}$R$_{13}$, —C(═O)R$_{12}$, —C(═O)OR$_{12}$, —C(═O)NR$_{12}$,R$_{13}$, —NR$_{12}$C(═O)R$_{13}$, —S(O)$_2$R$_{14}$, —NR$_{12}$SO$_2$R$_{14}$, and 5- to 6-membered heteroaryl substituted with C$_{1-3}$alkyl group.

Embodiment 6: a compound as defined in Embodiments 1-5, or an enantiomer, diastereomer, tautomer, or a pharmaceutically-acceptable salt thereof, wherein:

R$_1$ is phenyl or pyridyl, each of which is substituted with zero to three substituents independently selected from F, Cl, —OCF$_3$, —NH$_2$,

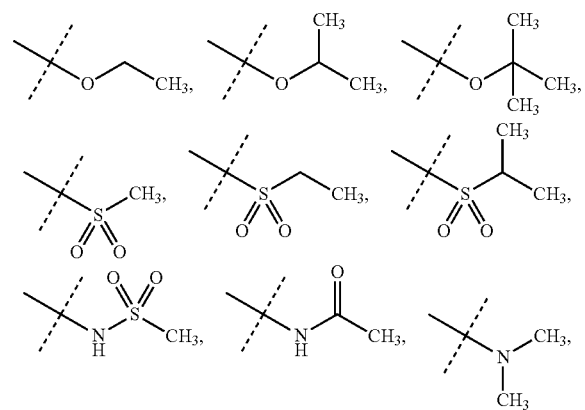

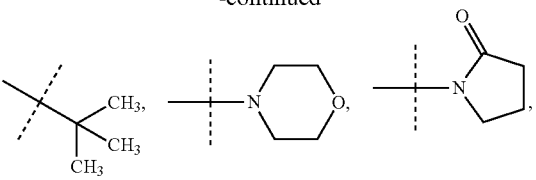

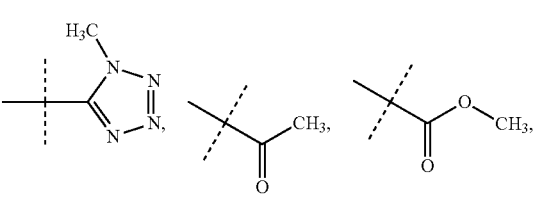

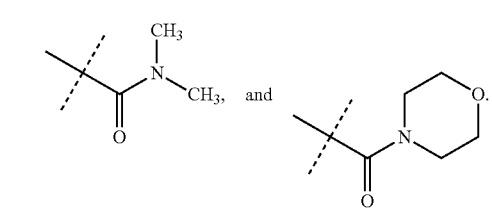

Embodiment 7: a compound as defined in Embodiments 1-6, or an enantiomer, diastereomer, tautomer, or a pharmaceutically-acceptable salt thereof, wherein:

W is N;
X is CH;
Y is CH; and
Z is N.

Embodiment 8: a compound as defined in Embodiments 1-7, or an enantiomer, diastereomer, tautomer, or a pharmaceutically-acceptable salt thereof, wherein:

W is CH;
X is CH;
Y is CH; and
Z is CH.

Embodiment 9: a compound as defined in Embodiments 1-8, or an enantiomer, diastereomer, tautomer, or a pharmaceutically-acceptable salt thereof, wherein:

W is CH;
X is CH;
Y is CH; and
Z is N.

Embodiment 10: a compound as defined in Embodiments 1-9, or an enantiomer, diastereomer, tautomer, or a pharmaceutically-acceptable salt thereof, wherein:

W is CH;
X is N;
Y is CH; and
Z is N.

Embodiment 11: a compound as defined in Embodiments 1-10, or an enantiomer, diastereomer, tautomer, or a pharmaceutically-acceptable salt thereof, wherein:

R₁ is

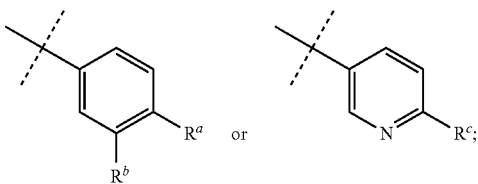

Rᵃ is H, —OCF₃, —NH₂,

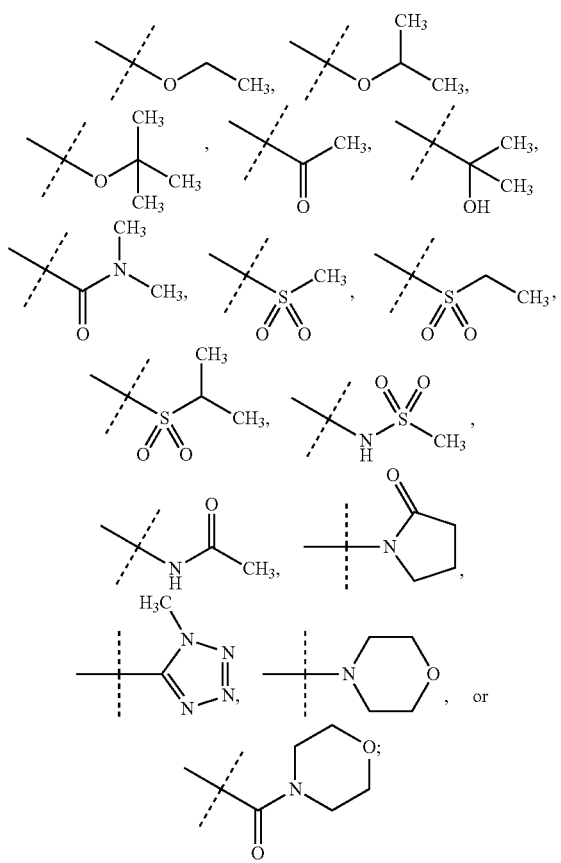

Rᵇ is H, F, or Cl; and
Rᶜ is H, F,

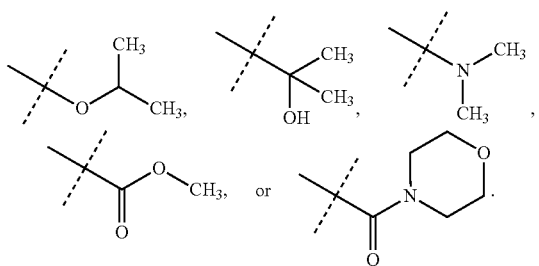

Embodiment 12: a compound, or an enantiomer, diastereomer, tautomer, or a pharmaceutically-acceptable salt thereof, selected from: (S)-(4-(5-(2-(1H-imidazo[4,5-b]pyrazin-2-yl)propan-2-yl)-9-fluoro-5H-chromeno[2,3-b]pyridin-2-yl)phenyl)(morpholino)methanone (1); (S)-1-(4-(5-(2-(1H-imidazo[4,5-b]pyrazin-2-yl)propan-2-yl)-9-fluoro-5H-chromeno[2,3-b]pyridin-2-yl)phenyl)ethanone (2); (S)-2-(4-(5-(2-(1H-imidazo[4,5-b]pyrazin-2-yl)propan-2-yl)-9-fluoro-5H-chromeno[2,3-b]pyridin-2-yl)phenyl)propan-2-ol (3); (S)-4-(5-(2-(1H-imidazo[4,5-b]pyrazin-2-yl)propan-2-yl)-9-fluoro-5H-chromeno[2,3-b]pyridin-2-yl)-N,N-dimethylbenzamide (4); (S)-5-(2-(1H-imidazo[4,5-b]pyrazin-2-yl)propan-2-yl)-9-fluoro-2-(4-(methylsulfonyl)phenyl)-5H-chromeno[2,3-b]pyridine (5); (S)-5-(2-(1H-imidazo[4,5-b]pyrazin-2-yl)propan-2-yl)-2-(4-(ethylsulfonyl)phenyl)-9-fluoro-5H-chromeno[2,3-b]pyridine (6); (S)-5-(2-(1H-imidazo[4,5-b]pyrazin-2-yl)propan-2-yl)-9-fluoro-2-(4-(isopropylsulfonyl)phenyl)-5H-chromeno[2,3-b]pyridine (7); (S)-5-(2-(1H-imidazo[4,5-b]pyrazin-2-yl)propan-2-yl)-9-fluoro-2-(4-isopropoxyphenyl)-5H-chromeno[2,3-b]pyridine (8); (S)-5-(2-(1H-imidazo[4,5-b]pyrazin-2-yl)propan-2-yl)-2-(3-chloro-4-isopropoxyphenyl)-9-fluoro-5H-chromeno[2,3-b]pyridine (9); (S)-5-(2-(1H-imidazo[4,5-b]pyrazin-2-yl)propan-2-yl)-9-fluoro-2-(3-fluoro-4-isopropoxyphenyl)-5H-chromeno[2,3-b]pyridine (10); (S)-5-(2-(1H-imidazo[4,5-b]pyrazin-2-yl)propan-2-yl)-2-(4-tert-butoxyphenyl)-9-fluoro-5H-chromeno[2,3-b]pyridine (11); (S)-5-(2-(1H-imidazo[4,5-b]pyrazin-2-yl)propan-2-yl)-2-(4-ethoxyphenyl)-9-fluoro-5H-chromeno[2,3-b]pyridine (12); (S)-5-(2-(1H-imidazo[4,5-b]pyrazin-2-yl)propan-2-yl)-9-fluoro-2-(4-(trifluoromethoxy)phenyl)-5H-chromeno[2,3-b]pyridine (13); (S)-(4-(5-(2-(1H-benzo[d]imidazol-2-yl)propan-2-yl)-9-fluoro-5H-chromeno[2,3-b]pyridin-2-yl)phenyl)(morpholino)methanone (14); (S)-(4-(5-(2-(3H-imidazo[4,5-b]pyridin-2-yl)propan-2-yl)-9-fluoro-5H-chromeno[2,3-b]pyridin-2-yl)phenyl)(morpholino)methanone (15); (S)-(4-(5-(2-(9H-purin-8-yl)propan-2-yl)-9-fluoro-5H-chromeno[2,3-b]pyridin-2-yl)phenyl)(morpholino)methanone (16); (S)-5-(2-(9H-purin-8-yl)propan-2-yl)-9-fluoro-2-(4-(methylsulfonyl)phenyl)-5H-chromeno[2,3-b]pyridine (17); (S)-5-(2-(1H-imidazo[4,5-b]pyrazin-2-yl)propan-2-yl)-9-fluoro-2-(4-morpholinophenyl)-5H-chromeno[2,3-b]pyridine (18); (S)-N-(4-(5-(2-(1H-imidazo[4,5-b]pyrazin-2-yl)propan-2-yl)-9-fluoro-5H-chromeno[2,3-b]pyridin-2-yl)phenyl)acetamide (19); (S)-5-(2-(1H-imidazo[4,5-b]pyrazin-2-yl)propan-2-yl)-9-fluoro-2-phenyl-5H-chromeno[2,3-b]pyridine (20); (S)-5-(2-(1H-imidazo[4,5-b]pyrazin-2-yl)propan-2-yl)-9-fluoro-2-(pyridin-4-yl)-5H-chromeno[2,3-b]pyridine (21); (S)-4-(5-(2-(1H-imidazo[4,5-b]pyrazin-2-yl)propan-2-yl)-9-fluoro-5H-chromeno[2,3-b]pyridin-2-yl)aniline (22); (S)-N-(4-(5-(2-(1H-imidazo[4,5-b]pyrazin-2-yl)propan-2-yl)-9-fluoro-5H-chromeno[2,3-b]pyridin-2-yl)phenyl)methanesulfonamide (23); (S)-1-(4-(5-(2-(1H-imidazo[4,5-b]pyrazin-2-yl)propan-2-yl)-9-fluoro-5H-chromeno[2,3-b]pyridin-2-yl)phenyl)pyrrolidin-2-one (24); (S)-5-(2-(1H-imidazo[4,5-b]pyrazin-2-yl)propan-2-yl)-9-fluoro-2-(6-isopropoxypyridin-3-yl)-5H-chromeno[2,3-b]pyridine (25); (S)-methyl 5-(5-(2-(1H-imidazo[4,5-b]pyrazin-2-yl)propan-2-yl)-9-fluoro-5H-chromeno[2,3-b]pyridin-2-yl)picolinate (26); S)-2-(5-(5-(2-(1H-imidazo[4,5-b]pyrazin-2-yl)propan-2-yl)-9-fluoro-5H-chromeno[2,3-b]pyridin-2-yl)pyridin-2-yl)propan-2-ol (27); (S)-5-(2-(1H-imidazo[4,5-b]pyrazin-2-yl)propan-2-yl)-9-fluoro-2-(6-fluoropyridin-3-yl)-5H-chromeno[2,3-b]pyridine (28); (S)-5-(5-(2-(1H-imidazo[4,5-b]pyrazin-2-yl)propan-2-yl)-9-fluoro-5H-chromeno[2,3-b]pyridin-2-yl)-N,N-dimethylpyridin-2-amine (29); (S)-(5-(5-(2-(1H-imidazo[4,5-b]pyrazin-2-yl)propan-2-yl)-9-fluoro-5H-chromeno[2,3-b]pyridin-2-yl)pyridin-2-yl)(morpholino)methanone (30); and (S)-5-(2-(1H-imidazo[4, 5-b]pyrazin-2-yl)propan-2-yl)-9-fluoro-2-(4-(1-methyl-1H-tetrazol-5-yl)phenyl)-5H-chromeno[2,3-b]pyridine (31).

Embodiment 13: a compound as defined in Embodiments 1-12, or an enantiomer, diastereomer, tautomer, or a pharmaceutically-acceptable salt thereof, wherein:

$R_1$, $R_2$, $R_4$, $R_5$, $R_6$, $R_7$, and $R_8$ are the same or different and at each occurrence are independently selected from (i) hydrogen, halogen, alkyl, substituted alkyl, alkenyl, substituted alkenyl, alkynyl, substituted alkynyl, alkoxy, substituted alkoxy, nitro, cyano, $OR_{12}$, $-NR_{12}R_{13}$, $-C(=O)R_{12}$, $-CO_2R_{12}$, $-C(=O)NR_{12}R_{13}$, $-OC(=O)NR_{12}R_{13}$,

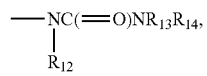

$-OC(=O)R_{12}$, $-NR_{12}C(=O)R_{13}$, $-NR_{12}C(O)OR_{13}$, $-NR_{12}C(S)OR_{13}$, $-S(O)_pR_{14}$, $NR_{12}SO_2R_{14}$, dialkylaminoalkoxy, alkoxyalkyloxyalkyloxy, $SO_2NR_{12}R_{13}$, $C_{3-6}$cycloalkyl, $C_{3-6}$cycloalkenyl, $C_{3-6}$cycloalkynyl, heterocyclo, aryl, and heteroaryl; and/or (ii) where possible, together with the atoms to which they are attached, each one of $R_1$, $R_2$, $R_4$, $R_5$, $R_7$, and $R_8$ is taken together with any one of $R_1$, $R_2$, $R_4$, $R_5$, $R_7$, and $R_8$ located on an adjacent atom to form a fused ring;

$R_{12}$ and $R_{13}$ are the same or different and at each occurrence are independently selected from hydrogen, alkyl, substituted alkyl, alkenyl, substituted alkenyl, alkynyl, substituted alkynyl, cycloalkyl, cycloalkenyl, aryl, heteroaryl, and heterocyclo;

p is 0, 1 or 2.

Embodiment 14: a compound as defined in Embodiments 1-3, or an enantiomer, diastereomer, tautomer, or a pharmaceutically-acceptable salt thereof, wherein $R_1$, $R_2$, $R_7$ and $R_8$ are each hydrogen.

Embodiment 15: the compound as defined in Embodiments 1-4, or an enantiomer, diastereomer, tautomer, or a pharmaceutically-acceptable salt, thereof, wherein $R_1$ is selected from hydrogen, alkyl, alkenyl, aryl, substituted aryl, cyano, $CF_3$, alkoxy, halogen, hydroxyl, dialkylamino, monoalkylamino, dialkylaminoalkoxy, alkoxyalkoxyalkoxy, and a 4- to 7-membered heterocyclo having one to three heteroatoms selected from O, S and N. Preferred compounds are those where $R_1$ is hydrogen, $C_{1-6}$alkyl, halogen, cyano, $-SC_{1-6}$alkyl, $C_{2-6}$alkenyl, (un)substituted phenyl, $(C_{1-6}$alkyl$)_{1-2}$amino, and a 5- to 6-membered heterocyclo having one to three heteroatoms selected from O, S, and N. Especially preferred compounds are those where $R_1$ is substituted phenyl.

Embodiment 16: a compound as defined in Embodiments 1-5, or an enantiomer, diastereomer, tautomer, or a pharmaceutically-acceptable salt thereof, wherein $R_5$ is selected from hydrogen, haloalkyl, alkoxy, haloalkoxy, halogen, amino, dialkylamino, heterocyclo, phenyl, and halophenyl.

Embodiment 17: a compound as defined in Embodiments 1-6, or an enantiomer, diastereomer, tautomer, or a pharmaceutically-acceptable salt thereof, wherein $R_1$ is selected from 5- to 10-membered aryl and 5- to 10-membered heteroaryl, wherein said aryl and heteroaryl group are each substituted with zero to three substituents independently selected from halogen, $C_{1-6}$hydroxyalkyl, $-OR_{12}$, $-NR_{12}R_{13}$, $-C(=O)R_{12}$, $-C(=O)OR_{12}$, $-C(=O)NR_{12}R_{13}$, $-NR_{12}C(=O)R_{13}$, $-S(O)_2R_{14}$, $-NR_{12}SO_2R_{14}$, and 5- to 6-membered heteroaryl substituted with $C_{1-3}$alkyl group; and $R_5$ is fluoro, chloro, or dimethylamino.

Embodiment 18: a compound as defined in Embodiments 1-7, or an enantiomer, diastereomer, tautomer, or a pharmaceutically-acceptable salt thereof, wherein:

$R_9$ and $R_{10}$ are each independently selected from methyl, or combined with the carbon they are attached to form cyclopropyl, cyclobutyl, and cyclopentyl, and especially wherein $R_9$ and $R_{10}$ are each methyl.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula I, or an enantiomer, diastereomer, or a pharmaceutically-acceptable salt, and a pharmaceutically acceptable carrier therefore.

Other embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder, wherein the disease or disorder is selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease.

In still another embodiment, the present invention provides a method of treating endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, a disease associated with the expression product of a gene whose transcription is stimulated or repressed by glucocorticoid receptors, or a disease associated with AP-1- and/or NFκB-induced transcription, or a disease associated with AP-1 and/or NFκB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula I of the invention to a patient.

Other embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder wherein the disease or disorder is selected from a metabolic disease or an inflammatory or immune disease comprising the administration to a patient in need of treatment, a therapeutically effective amount of a compound of formula I.

A more preferred embodiment of the present invention provides 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder wherein the disease or disorder is selected from a metabolic disease wherein the disease is a metabolic disease selected from Type I diabetes, Type II diabetes, juvenile diabetes, and obesity.

Other preferred embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder, wherein the disease or disorder is an inflammatory or immune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis, eczema, seborrhoea, pulmonary inflammation, eye uveitis, hepatitis, Graves' disease, Hashimoto's thyroiditis, autoimmune thyroiditis, Behcet's or Sjögren's syndrome, pernicious or immunohaemolytic anemia, atherosclerosis, Addison's disease, idiopathic adrenal insufficiency, autoimmune polyglandular disease, glomerulonephritis, scleroderma, morphea, lichen planus, vitiligo, alopecia areata, autoimmune alopecia, autoimmune hypopituitarism, Guillain-Barre syndrome, alveolitis, contact hypersensitivity, delayed-type hypersensitivity, contact dermatitis, urticaria, skin allergies, respiratory allergies, hay fever, gluten-sensitive enteropathy, osteoarthritis, acute pancreatitis, chronic pancreatitis, acute respiratory distress syndrome, Sezary's syndrome, restenosis, stenosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

Especially preferred embodiments are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder where the disease or disorder is selected from transplant rejection, rheumatoid arthritis, psoriatic arthritis, multiple sclerosis, asthma, inflammatory bowel disease, systemic lupus erythematosis, and psoriasis.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

In still another embodiment, the present invention provides a pharmaceutical combination comprising one or more compounds of Formula I and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

Even more preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD 1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, AXOKINE®, dexamphetamine, phentermine, phenylpropanolamine, and/or mazindol, wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*, R*)]-hexahydro-6-[(2-mercapto-1-oxo-3-phenylpropyl) amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The term "disease associated with GR transactivation", as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary adrenocortical insufficiency, and Addison's disease.

The term "treat", "treating", or "treatment", in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR", as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger et al., *Science*, 228:740-742 (1985), and in Weinberger et al., *Nature*, 318:670-672 (1986); rat glucocorticoid receptor as disclosed in Miesfeld, R., *Nature*, 312:779-781 (1985); mouse glucocorticoid receptor as disclosed in Danielson, M. et al., *EMBO J.*, 5:2513; sheep glucocorticoid receptor as disclosed in Yang, K. et al., *J. Mol. Endocrinol.*, 8:173-180 (1992); marmoset glucocorticoid receptor as disclosed in Brandon, D. D. et al., *J. Mol. Endocrinol.*, 7:89-96 (1991); and human GR-beta as disclosed in Hollenberg, S. M. et al., *Nature*, 318:635 (1985); Bamberger, C. M. et al., *J. Clin. Invest.*, 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjögren's syndrome (dry eyes/mouth), pernicious or immunohaemolytic anemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (depigmentation of the skin), alopecia areata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), urticaria, skin allergies, respiratory allergies (hay fever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis.

Methods of Preparation

Compounds of the present invention may be synthesized by many methods known to those skilled in the art of organic chemistry. Accordingly, the synthetic schemes described below are illustrative only as additional methods of preparing compounds of the present invention will be evident to those skilled in the art. Likewise, it will be apparent to one of skill in the art that various steps in the synthetic schemes may be performed in an alternate sequence to give the desired compound or compounds. Exemplified compounds are typically prepared as racemic mixtures. Homochiral compounds may be prepared by techniques known to one skilled in the art, for example, by the separation of racemic products by chiral phase preparative HPLC. Enantiomerially enriched compounds may be prepared by known methods including, but not limited to, the incorporation of chiral auxiliary functionalities into racemic intermediates providing enantio-enriched products upon cleavage of the chiral auxiliary.

More specifically, the compounds of the invention may be prepared by the exemplary processes described in the following reaction Schemes A-C. Exemplary reagents and procedures for these reactions appear hereinafter. Starting materials are commercially available or can be readily prepared by one of ordinary skill in the art. For all of the schemes, the groups W, X, Y, Z, P, $R_1$, $R_2$, $R_3$, $R_4$, $R_5$, $R_6$, $R_7$, $R_8$, $R_9$, $R_{10}$, $R_{11}$, $R_{12}$, and $R_{13}$, are as described herein for a compound of formula I, unless otherwise indicated.

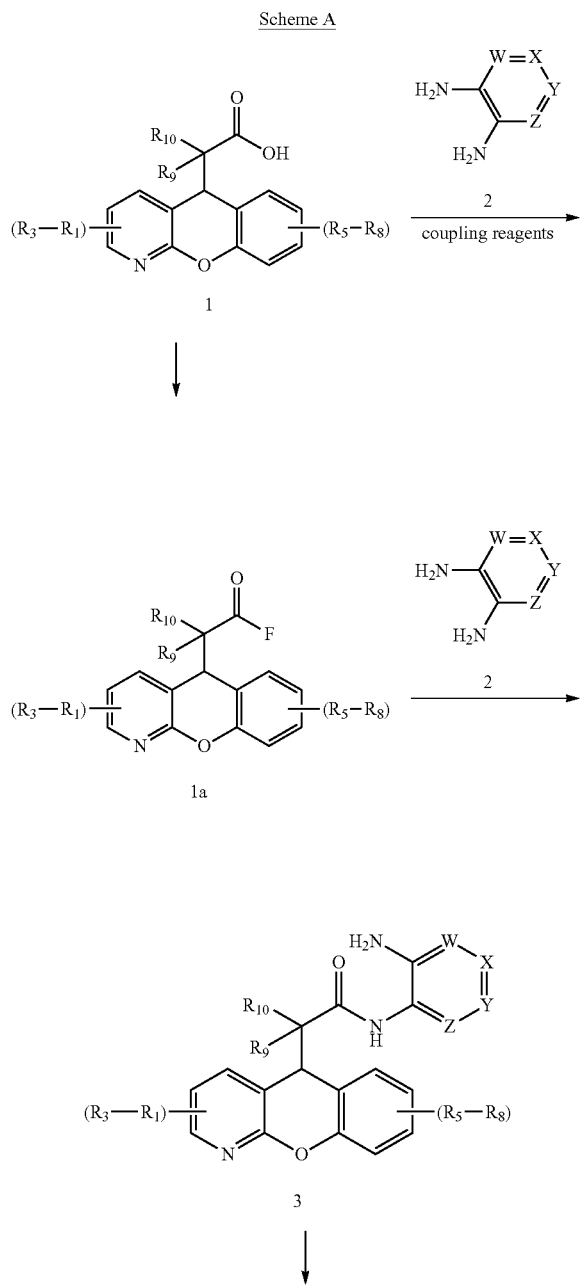

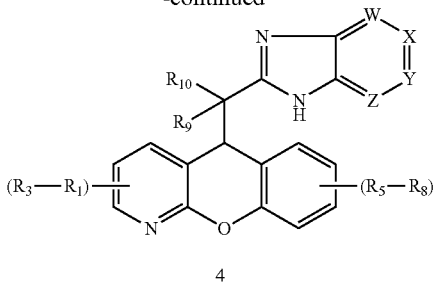

As illustrated in Scheme A, compounds of Formula (3) can be prepared from carboxylic acid 1 or acyl fluoride 1a with commercially available aniline 2 using amide bond syntheses known in the art, including methods commonly used in peptide syntheses, such as HATU, BOP, and DCC-mediated couplings: a) Synthesis, 453 (1972); b) *J. Org. Chem.*, 59:3275 (1994). Acyl fluoride 1a can be prepared from acid 1 under reaction conditions see: a) *J. Am. Chem. Soc.*, 112:9651 (1990); b) *Tetrahedron Lett.*, 32:1303 (1991). Compounds of formula (4) could be prepared from intermediate 3 under acidic conditions see: a) *Bioorg. Med. Chem. Lett.*, 18(14):3955 (2008); b) *Tetrahedron Lett.*, 49(43):6231 (2008). It is understood that these references are only illustrative; however, numerous references are known in the literature which could provide the desired transformations-described above.

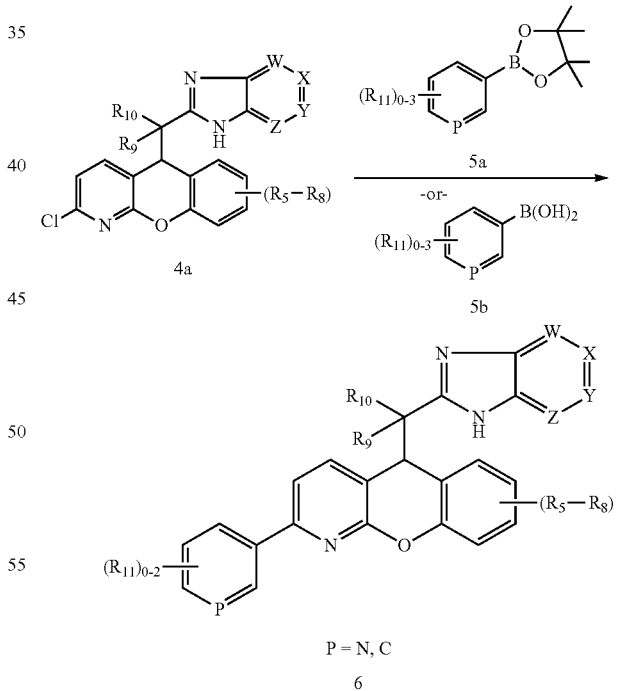

Chloro-derivatives having the formula (a) can be transformed into biaryl compounds having the formula (6) by reaction with an aromatic or heteroaromatic boronic acid-derivatives 5a and 5b in the presence of a palladium catalyst (such as Pd(PPh$_3$)$_4$) and a base (such as K$_2$CO$_3$ or Na$_2$CO$_3$) in an appropriate solvent (such as toluene, DMF, DME or water), under conventional Suzuki coupling conditions see: *Synth. Commun.*, 11:513 (1981).

coupling conditions. As will be recognized by those skilled in the art, a variety of procedures for the synthesis of amides

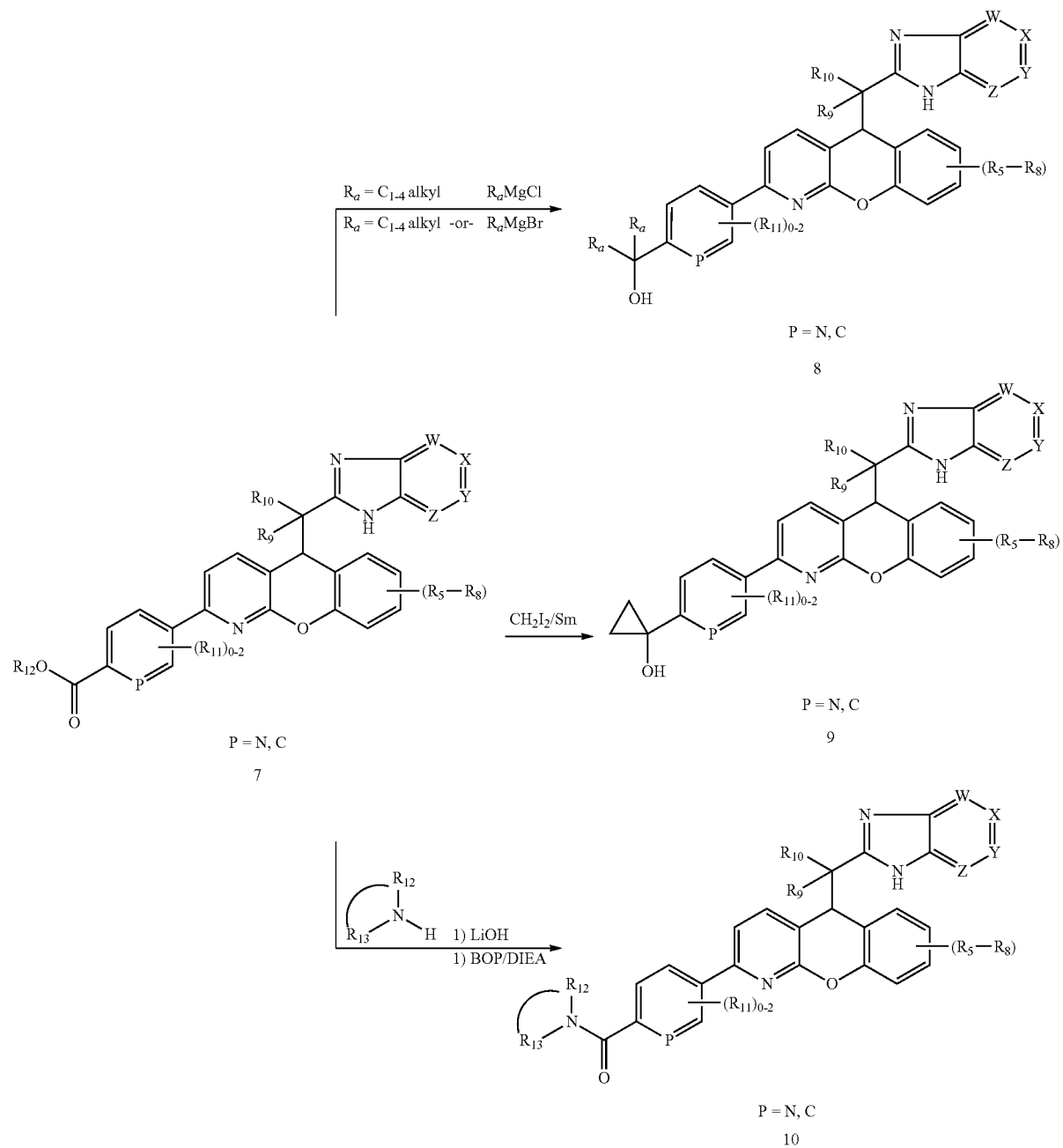

Scheme C

Compounds of formula (8), (9), and (10) as shown in Scheme C can be prepared from intermediate (7) by a number of known procedures in the literature. For example, intermediate 7 can be transformed into compounds of formula (8) by reacting with MeMgCl in a solvent such as THF. See, for example, *Org. Synth.* (II), 602 (1943). Compounds of formula (9) can be prepared from the ester 7 under reaction conditions see: *Tetrahedron Lett.*, 30(38):5149 (1989). Conversion of the ester 7 to an amide 10 can be accomplished by a LiOH-promoted deprotection step followed by an amino acid coupling step using standard from carboxylic acids are known (see, for example, Pennington, M. W. et al., eds., *Methods in Molecular Biology*, Vol. 35: Peptide Synthesis Protocols, Humana Press (1994), and the skilled practitioner will adjust the methods, reagents, and conditions to the example at hand.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy ($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), $-NR_aR_b$, $-N(\text{alkyl})_3^+$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$, $-OC(O)R_a$, $-C(=O)R_a$, $-CO_2R_a$, $-C(=O)NR_aR_b$, $-C(=O)(C_{1-4}\text{alkylene})NR_aR_b$, $-C(=O)NR_a(SO_2)R_b$, $-CO_2(C_{1-4}\text{alkylene})NR_aR_b$, $-NR_aC(=O)R_b$, $-NR_aCO_2R_b$, $-NR_a(C_{1-4}\text{alkylene})CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2$(alkyl), $C_{3-7}$cycloalkyl, phenyl, benzyl, phenylethyl, naphthyl, a four- to seven-membered heterocyclo, or a five- to six-membered heteroaryl, or when attached to the same nitrogen atom may join to form a heterocyclo or heteroaryl, and R is selected from same groups as $R_a$ and $R_b$ but is not hydrogen. Each group $R_a$ and $R_b$ when other than hydrogen, and each R group optionally has up to three further substituents attached at any available carbon or nitrogen atom of $R_a$, $R_b$, and/or $R_c$, said substituent(s) being selected from the group consisting of ($C_{1-6}$)alkyl, ($C_{2-6}$)alkenyl, hydroxy, halogen, cyano, nitro, =O (as valence allows), $CF_3$, $O(C_{1-6}\text{alkyl})$, $OCF_3$, $C(=O)H$, $C(=O)(C_{1-6}\text{alkyl})$, $CO_2H$, $CO_2(C_{1-6}\text{alkyl})$, $NHCO_2(C_{1-6}\text{alkyl})$, $-S(C_{1-6}\text{alkyl})$, $-NH_2$, $NH(C_{1-6}\text{alkyl})$, $N(C_{1-6}\text{alkyl})_2$, $N(CH_3)_3^+$, $SO_2(C_{1-6}\text{alkyl})$, $C(=O)(C_{1-4}\text{alkylene})NH_2$, $C(=O)(C_{1-4}\text{alkylene})NH(\text{alkyl})$, $C(=O)(C_{1-4}\text{alkylene})N(C_{1-4}\text{alkyl})_2$, $C_{3-7}$cycloalkyl, phenyl, benzyl, phenylethyl, phenyloxy, benzyloxy, naphthyl, a four- to seven-membered heterocyclo or cycloalkyl, or a five- to six-membered heteroaryl. When a substituted alkyl is substituted with an aryl (including, for example, phenyl and naphthyl), heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

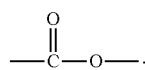

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—$(CH_2)_{1-5}$NH—$CH_2$—, —O—$(CH_2)_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, $CH_2$—O—$CH_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —C(=O)—, —C(=O)$NR_d$—, —C(=S)$NR_d$—, —$SO_2$—, —$SO_2NR_d$—, —$CO_2$—, or —$NR_dCO_2$—; $A_2$ is a bond, $C_{1-3}$alkylene, $C_{2-3}$alkenylene, —$C_{1-4}$alkylene-$NR_d$—, —$C_{1-4}$alkylene-$NR_dC(=O)$—, —$C_{1-4}$alkylene-S—, —$C_{1-4}$alkylene-$SO_2$—, or —$C_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—$C_{1-6}$alkyl.

The term "alkylthio" refers to a sulfur atom that is substituted by an alkyl or substituted alkyl group as defined herein. For example, the term "thioalkyl" includes the group —S—$C_{1-6}$alkyl, and so forth.

The term "alkylamino" refers to an amino group substituted with an alkyl group or substituted alkyl group as defined above. For example, the term "alkylamino" includes the group —NR—$C_{1-12}$alkyl (where R is preferably hydrogen but may include alkyl or substituted alkyl as defined above).

When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —$CH_2$—N($CH_3$)$_2$, and —($CH_2$)$_2$—$NH_2$. A lower aminoalkyl comprises an aminoalkyl having one to four carbon atoms. The term ($C_{1-4}$ alkyl)$_{0-2}$amino includes the groups $NH_2$, —NH($C_{1-4}$alkyl), and —N($C_{1-4}$alkyl)$_2$. "Amino" used by itself refers to the group $NH_2$. A "substituted amino" refers to an amino group substituted as described above for the nitrogen atom of a heteroalkylene chain and includes, for example, the terms alkylamino and acylamino (—$NR_d$C(O)$R_e$). Where amino is designated as mono-substituted without further definition, the extra nitrogen valence is hydrogen. For example, the term "alkylaminocarbonyl(halo)$_{0-1}$aryl" describes a group of the general formula:

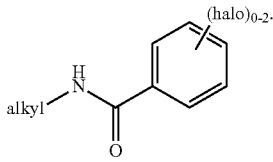

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, whereas a bivalent alkoxy includes groups such as —O—$C_{1-12}$alkylene-.

It should be understood that the selections for all groups, including for examples, alkoxy, thioalkyl, and aminoalkyl, will be made by one skilled in the field to provide stable compounds. Thus, for example, in compounds of formula I, when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "carbonyl" refers to a bivalent carbonyl group —C(=O)—. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is a heterocyclo, such as morpholinyl.

The term "acyl" refers to a carbonyl group linked to an organic radical, more particularly, the group C(=O)$R_e$. The group $R_e$ can be selected from alkyl, alkenyl, alkynyl, aminoalkyl, substituted alkyl (i.e., substituted alkylene), substituted alkenyl, substituted alkynyl, cycloalkyl, heterocyclo, aryl, or heteroaryl, as defined herein. When $R_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

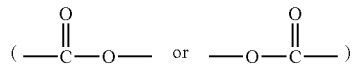

linked to an organic radical (CO$_2$R$_e$), as well as the bivalent groups —CO$_2$—, —CO$_2$R$_e$— which are linked to organic radicals in compounds of formula I, wherein Re is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.) Accordingly, in compounds of formula I, when it is recited that G can be "alkoxycarbonyl", this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "sulfonyl" refers to a sulphoxide group (—S(O)$_2$—) linked to an organic radical in compounds of formula I, more particularly, the monovalent group —S(O)$_2$—R$_e$. Likewise, the term "sulfinyl" refers to the group (—S(O)—) linked to an organic radical in compounds of formula I, more particularly, the monovalent group —S(O)—R$_e$. Additionally, the sulfonyl or sulfinyl group may be bivalent, in which case R$_e$ is a bond. The group Re is selected from those recited above for acyl and alkoxycarbonyl groups, with the exception that R$_e$ is not hydrogen.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$ —SO$_2$NR$_a$R$_b$, —SO$_2$NR$_a$C(=O) R$_b$, SO$_3$H, —PO(OH)$_2$, —C(=O)R$_a$, —CO$_2$R$_a$, —C(=O) NR$_a$R$_b$, —C(=O)(C$_{1-4}$alkylene)NR$_a$R$_b$, —C(=O)NR$_a$ (SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}$alkyl), $OCF_3$, $C(\!=\!O)H$, $C(\!=\!O)(C_{1-4}$alkyl), $CO_2H$, $CO_2(C_{1-4}$alkyl), $NHCO_2$ $(C_{1-4}$alkyl), $-S(C_{1-4}$alkyl), $-NH_2$, $NH(C_{1-4}$alkyl), $N(C_{1-4}$alkyl$)_2$, $N(C_{1-4}$alkyl$)_3^+$, $SO_2(C_{1-4}$alkyl), $C(\!=\!O)$ $(C_{1-4}$alkylene)$NH_2$, $C(\!=\!O)(C_{1-4}$alkylene)NH(alkyl), $C(\!=\!O)(C_{1-4}$alkylene)N$(C_{1-4}$alkyl$)_2$ and/or phenyl optionally substituted with any of the preceding groups. As valence allows, if said further ring is cycloalkyl or heterocyclo it is additionally optionally substituted with $=\!O$ (oxo).

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems,

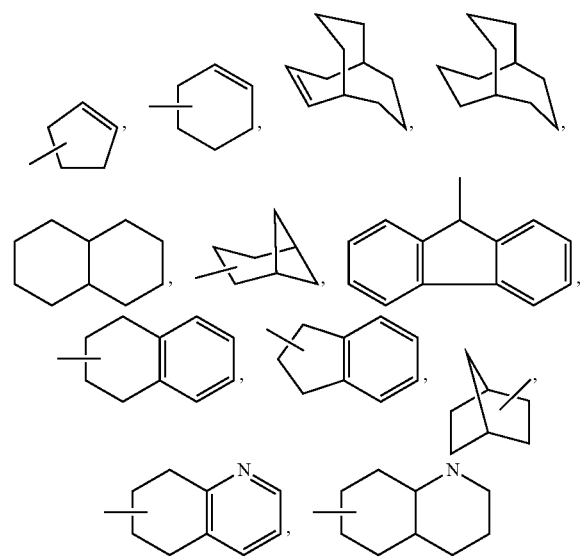

and the like, which optionally may be substituted at any available atoms of the ring(s). Preferred cycloalkyl groups include cyclopropyl, cyclopentyl, cyclohexyl, and

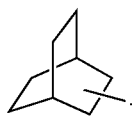

The term "halo" or "halogen" refers to chloro, bromo, fluoro and iodo.

The term "haloalkyl" means a substituted alkyl having one or more halo substituents. For example, "haloalkyl" includes mono-, bi-, and trifluoromethyl.

The term "haloalkoxy" means an alkoxy group having one or more halo substituents. For example, "haloalkoxy" includes $OCF_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, ($=\!S$), $SO_3H$, $-NR_aR_b$, $-N($alkyl$)_3^+$, $-NR_aSO_2$, $-NR_aSO_2R$, $-SO_2R_c$ $-SO_2NR_aR_b$, $-SO_2NR_aC(\!=\!O)R_b$, $SO_3H$, $-PO(OH)_2$, $-C(\!=\!O)R_a$, $-CO_2R_a$, $-C(\!=\!O)NR_aR_b$, $-C(\!=\!O)(C_{1-4}$alkylene)$NR_aR_b$, $-C(\!=\!O)NR_a(SO_2)R_b$, $-CO_2(C_{1-4}$alkylene)$NR_aR_b$, $-NR_aC(\!=\!O)R_b$, $-NR_aCO_2R_b$, $-NR_a(C_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}$alkyl), $OCF_3$, $C(\!=\!O)H$, $C(\!=\!O)$ $(C_{1-4}$alkyl), $CO_2H$, $CO_2(C_{1-4}$alkyl), $NHCO_2(C_{1-4}$alkyl), $-S(C_{1-4}$alkyl), $-NH_2$, $NH(C_{1-4}$alkyl), $N(C_{1-4}$alkyl$)_2$, $N(C_{1-4}$alkyl$)_3^+$, $SO_2(C_{1-4}$alkyl), $C(\!=\!O)(C_{1-4}$alkylene)$NH_2$, $C(\!=\!O)(C_{1-4}$alkylene)NH(alkyl), $C(\!=\!O)(C_{1-4}$alkylene)N $(C_{1-4}$alkyl$)_2$ and/or phenyl optionally substituted with any of the preceding groups. As valence allows, if said further ring is cycloalkyl or heterocyclo it is additionally optionally substituted with $=\!O$ (oxo).

Thus, examples of aryl groups include:

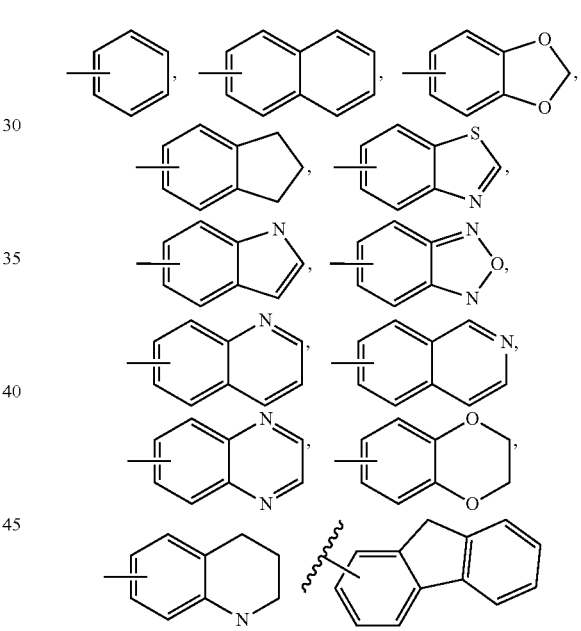

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$ $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Heterocyclo groups in compounds of formula I include N

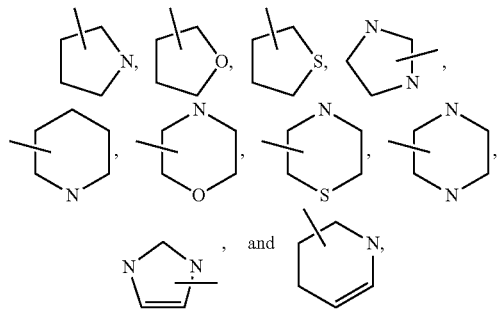

which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $-NR_aR_b$, $-N(alkyl)_3^+$, $-NR_aSO_2$, $-NR_aSO_2R_c$, $-SO_2R_c$ $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula I, preferred heteroaryl groups include

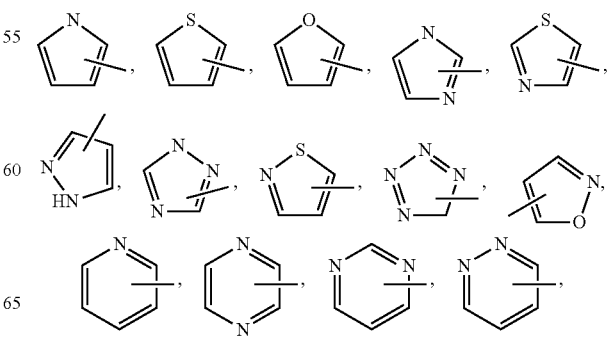

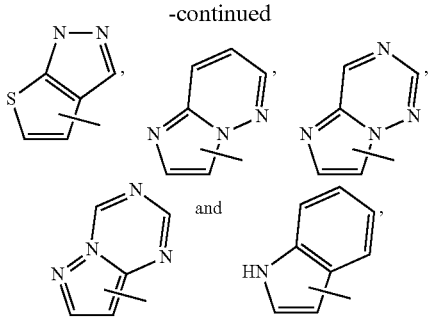

and the like, which optionally may be substituted at any available carbon or nitrogen atom. Aromatic rings may also be designated by an unbroken circle in the ring.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s)" may include zwitterions (inner salts), e.g., when a compound of formula I contains both a basic moiety, such as an amine or a pyridine or imidazole ring, and an acidic moiety, such as a carboxylic acid. Pharmaceutically acceptable (i.e., nontoxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates (e.g., hydrates) of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, antiobesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or RAPAMUNE®) or derivatives thereof, infliximab (REMICADE®, Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g., CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, PROGRAF®).

The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875 and 5,885,983, and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135, 5,712,279 and 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

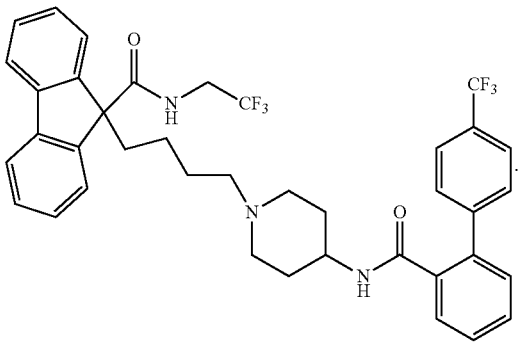 [SMILES: O=C(NC1CCN(CCCCC2(C(=O)NCC(F)(F)F)c3ccccc3-c3ccccc32)CC1)c1ccccc1-c1ccc(C(F)(F)F)cc1]

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphonosulfonates disclosed in U.S. Pat. No. 5,712,396, those disclosed by Biller et al., *J. Med. Chem.*, 31(10):1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987), and cyclopropanes reported by Capson, T. L., Ph.D., dissertation, Dept. Med. Chem., Univ. Utah, Abstract, Table of Contents, pp. 16, 17, 40-43, 48-51, Summary (June 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, *Drugs of the Future*, 24:9-15 (1999), (Avasimibe); Nicolosi et al., "The ACAT inhibitor, Cl-1011 is effective in the prevention and regression of aortic fatty streak area in hamsters", *Atherosclerosis* (Shannon, Irel)., 137(1):77-85 (1998), Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, pp. 173-198, Ruffolo, Jr., R. R. et al., eds., CRC Press, Inc., publ. (1995); Sliskovic et al., "ACAT inhibitors: potential anti-atherosclerotic agents", *Curr. Med. Chem.*, 1(3):204-225 (1994); Stout, D. M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity. Inhibitors of Acyl-CoA:Cholesterol Acyltransferase (ACAT). 7. Development of a Series of Substituted N-Phenyl-N'-[(1-phenylcyclopentyl)-methyl]ureas with Enhanced Hypocholestrolemic Activity", *Chemtracts-Organic Chemistry*, 8:359-362 (1995), or TS-962 (acetamide, N-[2,6-bis (1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis*, 115:45-63 (1995) and *J. Med. Chem.* 41:973 (1998).

The hypolipidemic agent may be an ileal Na+/bile acid cotransporter inhibitor such as disclosed in *Drugs of the Future*, 24:425-430 (1999).

The lipid-modulating agent may be a cholesteryl ester transfer protein (CETP) inhibitor such as Pfizer's CP 529, 414 (torcetrapib) (WO 00/38722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the *Physicians' Desk Reference* and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the *Physicians' Desk Reference*.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the *Physicians' Desk Reference*, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al., "Attenuation of diet-induced atherosclerosis in rabbits with a highly selective 15-lipoxygenase inhibitor lacking significant antioxidant properties", *Brit. J. Pharmacol.*, 120:1199-1206 (1997), and Cornicelli et al., "15-Lipoxygenase and its Inhibition: A Novel Therapeutic Target for Vascular Disease", *Current Pharmaceutical Design,* 5:11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone)

(Sankyo/WL), NN-2344 (balaglitazone) (Dr. Reddy/NN), or YM-440 ((Z)-1,4-bis-4-[(3,5-dioxo-1,2,4-oxadiazolidin-2-yl-methyl)]-phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the *Physicians' Desk Reference* (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the *Physicians' Desk Reference*.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]- (Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes, 47:1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO 99/38501, WO 99/46272, WO 99/67279 (PROBIODRUG), WO 99/67278 (PROBIODRUG), WO 99/61431 (PROBIODRUG), saxagliptin (preferred), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., Biochemistry, 38(36): 11597-11603 (1999), TSL-225 (tryptophyl-1,2,3,4-tetrahydro-isoquinoline-3-carboxylic acid (disclosed by Yamada et al., Bioorg. Med. Chem. Lett. 8:1537-1540 (1998), 2-cyanopyrrolidides and 4-cyanopyrrolidides as disclosed by Ashworth et al., Bioorg. Med. Chem. Lett., 6(22): 1163-1166 and 2745-2748 (1996) employing dosages as set out in the above references.

The meglitinide which may optionally be employed in combination with the compound of formula I of the invention may be repaglinide, nateglinide (Novartis) or KAD 1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benezenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may optionally be employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or AXOKINE® (Regeneron), with sibutramine and topiramate being preferred.

The thyroid receptor agonist which may be optionally employed in combination with a compound of formula I may be a thyroid receptor ligand as disclosed in WO 97/21993 (U. Cal SF), WO 99/00353 (KaroBio), WO 00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al. mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol., 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in Chemical Abstracts, 102:72588v, and Jpn. J. Pharmacol., 40:373 (1986); Ciba-Geigy's CGS 14824 (3-([1-ethoxycarbonyl-3-phenyl-(1S)-propyl]amino)-2,3,4,5-tetrahydro-2-oxo-1-(3 S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Ther. Res., 39:671 (1986); 40:543 (1986); ramipril (Hoechst) disclosed in European Patent No. 79-022 and Curr. Ther. Res., 40:74 (1986); Ru 44570 (Hoechst) disclosed in Arzneimittelforschung, 34:1254 (1985), cilazapril (Hoffman-LaRoche) disclosed in J. Cardiovasc. Pharmacol., 9:39 (1987); R 31-2201 (Hoffman-LaRoche) disclosed in FEBS Lett., 165:201 (1984); lisinopril (Merck), indalapril (delapril) disclosed in U.S. Pat. No. 4,385,051; indolapril (Schering) disclosed in J. Cardiovasc. Pharmacol., 5:643, 655 (1983), spirapril (Schering) disclosed in Acta. Pharmacol. Toxicol., 59(Supp. 5):173 (1986); perindopril (Servier) disclosed in Eur. J. Clin. Pharmacol., 31:519 (1987); quinapril (Warner-Lambert) disclosed in U.S. Pat. No. 4,344,949 and CI925 (Warner-Lambert) ([3 S-[2[R(*)R(*)]]3R(*)]-2-[2-[[1-(ethoxycarbonyl)-3-phenylpropyl]amino]-1-oxopropyl]-1,2,3,4-tetrahydro-6,7-dimethoxy-3-isoquinolinecarboxylic acid HCl) disclosed in Pharmacologist, 26:243, 266 (1984), WY-44221 (Wyeth) disclosed in J. Med. Chem., 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359 and 5,525,723, European Patent Application Nos. 0599444, 0481522, 0599444, 0595610, 0534363 A2, 534396, 534492 and 0629627 A2.

Preferred are those NEP/ACE inhibitors and dosages thereof which are designated as preferred in the above patents/applications which U.S. patents are incorporated herein by reference; most preferred are omapatrilat, BMS-189921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from about 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev) amlodipine besylate (NORVASC®), prazosin HCl (MINIPRESS®), verapamil, nifedipine, nadolol, diltiazem, felodipine, nisoldipine, isradipine, nicardipine, atenolol, carvedilol, sotalol, terazosin, doxazosin, propranolol, and clonidine HCl (CATAPRES®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (FOSAMAX®).

Dosages employed for the above drugs will be as set out in the *Physicians' Desk Reference.*

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (AVICEL®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human from about 0.1 to 500 mg/kg of body weight of active compound per day, or between 0.5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transcriptional assays.

Compounds of the invention, including the compounds described in the examples hereof, have been tested in at least one of the assay(s) described below and have glucocorticoid receptor (GR)/Dexamethasone (Dex) inhibition activity (>25% at 10 µM) and/or AP-1 inhibition activity ($EC_{50}$ less than 15 µM).

Identical and/or similar assays are described in U.S. application Ser. No. 10/621,807, filed Jul. 17, 2003 which is incorporated in its entirety herein by reference.

GR Binding Assays

Glucocorticoid Receptor Binding Assay (I)

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e., Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition is 0%. Test compounds were analyzed in the concentration range from 8.5E-05 µM to 5 µM.

Glucocorticoid Receptor Binding Assay (II)

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e., Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 2.4 nM to 40 µM.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e., are ligands for the specific NHR.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TOPCOUNT® luminescence counter. Repression of AP-1 activity was calculated as the percentage decrease in the signal induced by PMA alone. Test molecules were analyzed in the concentration range from 0.1 nM to 40 µM. $EC_{50}$s were determined by using standard curve fitting methods such as Excel fit (Microsoft Co.). An $EC_{50}$ is the test molecule concentration at which there is a 50% repression of the maximal inhibition of transcription, i.e., a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-κB-Luc, (Stratagene, LaJolla Calif.), and PMA or another stimulus, such as TNF-α or lipopolysaccharide, is used to activate the NF-κB pathway. NF-κB assays similar to that described in Yamamoto, K. et al., *J. Biol. Chem.*, 270(52):31315-31320 (Dec. 29, 1995) may be used.

The cellular transrepressional assays described above may be used to measure transrepression by any NHR. One of skill in the art will understand that assays may require the addition of components, such as a stimulus (e.g., PMA, lipopolysaccharide, TNF-α, etc) which will induce transcription mediated by AP-1 or NF-κB.

Additionally, AR mediated transrepression may be measured by the assay described in Palvimo, J. J. et al., *J. Biol. Chem.*, 271(39):24151-24156 (Sep. 27, 1996), and PR mediated transrepression may be measured by the assay described in Kalkhoven, E. et al., *J. Biol. Chem.*, 271(11): 6217-6224 (Mar. 15, 1996).

Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

EXAMPLES

The following Examples illustrate embodiments of the inventive compounds and starting materials, and are not intended to limit the scope of the claims. For ease of reference, the following abbreviations are used herein:

ABBREVIATIONS

AlCl₃=aluminum chloride
Ac₂O=acetic anhydride
AcONa=sodium acetate
bp=boiling point
CH₃CN=acetonitrile
DCC=dicyclohexylcarbodiimide
DCE=dichloroethane
DCM=dichloromethane
DMAP=4-dimethylaminopyridine
DIPEA or DIEA=N,N-diisopropylethylamine
DME=1,2-dimethoxyethane
DMF=dimethyl formamide
EDCI=1-3-dimethylaminopropyl)-3-ethylcarbodiimide
Et₂O=diethyl ether
HOBT=1-hydroxybenzotriazole
EtOAc=ethyl acetate
EtOH=ethanol
g=gram(s)
HCl=hydrochloric acid
KOH=potassium hydroxide
K₂CO₃=potassium carbonate
l=liter
LiAlH₄=lithium aluminum hydride
MeCN=acetonitrile
MeOH=methanol
MgSO₄=magnesium sulfate
NaH=sodium hydride
Na₂SO₄=sodium sulfate
NaOH=sodium hydroxide
NMP=1-methyl-2-pyrrolidinone
PBr₃=phosphorus tribromide
(Ph₃P)₄Pd=tetrakis(triphenylphosphine)palladium(0)
PS=polystyrene
SOCl₂=thionyl chloride
TEA=triethylamine
mg=milligram(s)
ml=milliliter
μl=microliter
mmol=millimole
μmol=micromole
mol=mole
mp=melting point
RT=room temperature Preparation 1

(S)-2-(2-Chloro-9-fluoro-5H-chromeno[2,3-b]pyridin-5-yl)-2-methylpropanoic acid

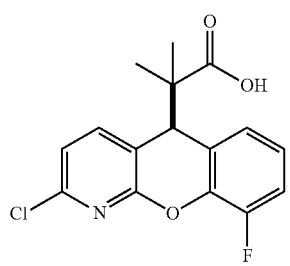 [SMILES: CC(C)(C(=O)O)[C@@H]1c2ccc(Cl)nc2Oc2c(F)cccc21]

The title compound was prepared by using the same procedures as described in PCT International Application No. WO 2008/021926 A2 (Feb. 21, 2008).

Preparation 2

(S)-2-(2-Chloro-9-fluoro-5H-chromeno[2,3-b]pyridin-5-yl)-2-methylpropanoyl fluoride

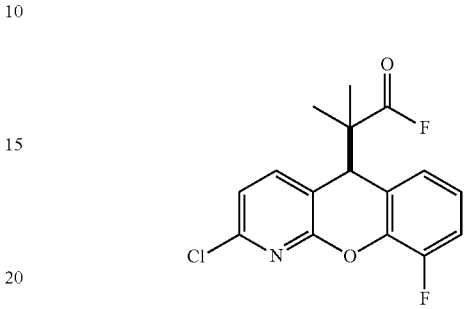

To a solution of (S)-2-(2-chloro-9-fluoro-5H-chromeno[2,3-b]pyridin-5-yl)-2-methylpropanoic acid (130 mg, 0.404 mmol) in DCM was added pyridine (0.037 mL, 0.455 mmol) and 2,4,6-trifluoro-1,3,5-triazine (63 mg, 0.467 mmol). The reaction mixture was stirred at r.t for 1 h and LC-MS indicated that the reaction was completed. The reaction mixture was diluted with AcOEt (50 mL), washed with saturated NH₄Cl (2×30 mL), dried over (Na₂SO₄), and concentrated under vacuo to give the above title compound which was used for the next reaction without further purification. LC-MS, 324 (M+1). HPLC: Rt=3.70 min. Method 1 Column:YMC S5 ODS-A 4.6×50 mm; Solvent A=10% MeOH–90% H₂O, 0.2% H₃PO₄; Solvent B=90% MeOH–10% H₂O, 0.2% H₃PO₄; 0% B to 100% B over 4 min with 1 min hold. ¹H NMR (400 MHz, chloroform-d) δ ppm 7.59 (1 H, d, J=7.9 Hz), 7.07-7.22 (3 H, m), 7.00 (1 H, d, J=7.5 Hz), 4.40 (1 H, s), 1.10 (6 H, d, J=17.6 Hz).

Preparation 3

(S)-5-(2-(1H-Imidazo[4,5-b]pyrazin-2-yl)propan-2-yl)-2-chloro-9-fluoro-5H-chromeno[2,3-b]pyridine

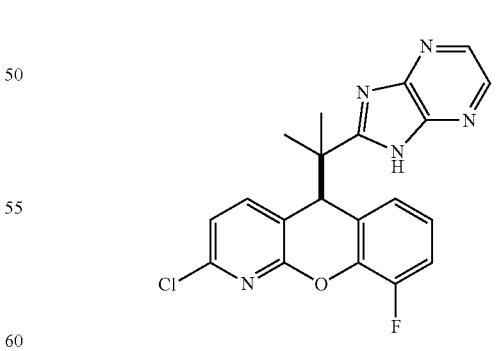

Step 1: To a solution of (S)-2-(2-chloro-9-fluoro-5H-chromeno[2,3-b]pyridin-5-yl)-2-methylpropanoyl fluoride (65 mg, 0.201 mmol) in MeCN was added pyridine (0.032 mL, 0.402 mmol), pyrazine-2,3-diamine (33.2 mg, 0.301 mmol), and the reaction mixture was stirred at r.t for 2 days. The reaction mixture was then stirred at 75° C. for 16 h. The reaction mixture was concentrated on the ROTAVAPOR® to dryness and used for next step without further purification. LC-MS, 414 (M+1).

Step 2: To a solution of above intermediate, (S)-N-(3-aminopyrazin-2-yl)-2-(2-chloro-9-fluoro-5H-chromeno[2,3-b]pyridin-5-yl)-2-methylpropanamide (71 mg, 0.172 mmol) was added $POCl_3$ (2 mL, 21.46 mmol), and stirred at reflux for 5 h. After cooling, the reaction mixture was poured into ice-water (30 mL). $Na_2CO_3$ was used to adjust the pH to basic (~9). The solution mixture was extracted with AcOEt, washed with saturated $NaHCO_3$ (2×30 mL), dried over ($Na_2SO_4$), and concentrated under vacuo to give the crude product which was purified with ISCO silica gel column (12 g, solvents: AcOEt/hexane=0%-45%, gradient time 20 min) to get the above title compound. LC-MS, 396 (M+1). HPLC: Rt=3.36 min. Method 1 Column:YMC S5 ODS-A 4.6×50 mm; Solvent A=10% MeOH–90% $H_2O$, 0.2% $H_3PO_4$; Solvent B=90% MeOH–10% $H_2O$, 0.2% $H_3PO_4$; 0% B to 100% B over 4 min with 1 min hold. $^1$H NMR (400 MHz, methanol-$d_3$) δ ppm 8.38 (2 H, s), 7.37 (1 H, d, J=7.9 Hz), 7.09-7.22 (2 H, m), 7.00 (1 H, td, J=8.1, 4.8 Hz), 6.74 (1 H, d, J=7.5 Hz), 4.64 (1 H, s), 1.37 (6 H, d, J=9.2 Hz).

Preparation 4

(S)-5-(2-(3H-Imidazo[4,5-b]pyridin-2-yl)propan-2-yl)-2-chloro-9-fluoro-5H-chromeno[2,3-b]pyridine

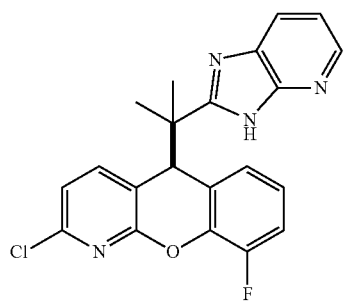 [SMILES: CC(C)(c1nc2cccnc2[nH]1)[C@@H]1c2ccc(Cl)nc2Oc2c(F)cccc21]

Step 1: To a solution of (S)-2-(2-chloro-9-fluoro-5H-chromeno[2,3-b]pyridin-5-yl)-2-methylpropanoic acid (500 mg, 1.554 mmol) in DMF, was added 2,3,4,5,6-pentafluorophenol (572 mg, 3.11 mmol) and DCC (481 mg, 2.331 mmol). The reaction mixture was stirred at r.t for 2 h before it was diluted with ethyl acetate (80 mL), washed with water (40 mL), saturated $NH_4Cl$ (2×40 mL), dried over ($Na_2SO_4$) and concentrated under reduced pressure. The residue was purified with Isco column (40 g, solvents: AcOEt/hexane: 0%-50%, gradient, 25 min). Peak 1 was identified as the desired product according to LC-MS, 488 (M+1).

Step 2: To a solution of the intermediate-derived from the previous step, (S)-perfluorophenyl 2-(2-chloro-9-fluoro-5H-chromeno[2,3-b]pyridin-5-yl)-2-methylpropanoate (667 mg, 1.367 mmol), in THF was added 3-nitropyridin-2-amine (476 mg, 3.42 mmol) and then KHMDS (4.10 mL, 4.10 mmol) at 0° C. The reaction mixture was stirred at r.t for o/n. The mixture was quenched with water (5 mL), diluted with AcOEt (100 mL), washed with saturated $NaHCO_3$ (2×30 mL), brine (30 mL), dried over ($Na_2SO_4$), and concentrated under vacuo to give the crude product which was purified with silica gel column (ISCO, 40 g, solvents: AcOEt/hexane=0%-35%, gradient: 30 min). LC-MS, 443 (M+1).

HPLC: Rt=3.45 min. Method 2 Column: CHROMOLITH® SpeedROD 4.6×50 mm; Solvent A=10% MeOH–90% $H_2O$, 0.2% $H_3PO_4$; Solvent B=90% MeOH–10% $H_2O$, 0.2% $H_3PO_4$; 0% B to 100% B over 4 min with 1 min hold. $^1$H NMR (400 MHz, methanol-$d_3$) δ ppm 8.69 (1 H, dd, J=4.8, 1.8 Hz), 8.44 (1 H, dd, J=8.3, 1.8 Hz), 7.78 (1 H, d, J=8.3 Hz), 7.46 (1 H, dd, J=8.3, 4.8 Hz), 7.24 (1 H, d, J=7.9 Hz), 7.12 (2 H, d, J=2.6 Hz), 4.67 (1 H, s), 1.06-1.18 (6 H, m).

Step 3: To a solution of the intermediate-derived from the previous step, (S)-2-(2-chloro-9-fluoro-5H-chromeno[2,3-b]pyridin-5-yl)-2-methyl-N-(3-nitropyridin-2-yl)propanamide (120 mg, 0.271 mmol), in DMF, was added $SnCl_2$-$2H_2O$ (2.71 mL, 2.71 mmol) (1M in DMF), and stirred at 35° C. for o/n. LC-MS indicated that only half material was converted. 5eq. of more $SnCl_2$-$2H_2O$ was added and the mixture was continued to stir at the same temperature for 20 h. The mixture was diluted with AcOEt (80 mL), water (40 mL), and filtered through a pad of CELITE®. The organic layer was collected, washed with saturated $NaHCO_3$ (2×30 mL), brine and dried over ($Na_2SO_4$). After concentration, the residue obtained was used to next step without further purification. LC-MS, 413 (M+1).

Step 4: To a solution of the intermediate-derived from the previous step, (S)-N-(3-aminopyridin-2-yl)-2-(2-chloro-9-fluoro-5H-chromeno[2,3-b]pyridin-5-yl)-2-methylpropanamide (100 mg, 0.242 mmol), was added $POCl_3$ (2 mL, 21.46 mmol) and stirred at r.t for 1 h and then stirred at 105° C. for 2 h. After cooling the mixture was poured into ice-water (30 mL), and $Na_2CO_3$ was used to adjust the pH to basic. The mixture was extracted with AcOEt (50 mL, 30 mL). The organic layer was collected, washed with saturated $NaHCO_3$ (30 mL), dried over ($Na_2SO_4$) and concentrated under vacuo to give the crude product which was purified with ISCO silica gel column (12 g, solvents: AcOEt/hexane=0%-65%, gradient time 25 min, then 65%) to get the above title compound. LC-MS, 395 (M+1). HPLC: Rt=2.70 min. Method 2 Column: CHROMOLITH® SpeedROD 4.6×50 mm; Solvent A=10% MeOH–90% $H_2O$, 0.2% $H_3PO_4$; Solvent B=90% MeOH–10% $H_2O$, 0.2% $H_3PO_4$; 0% B to 100% B over 4 min with 1 min hold. $^1$H NMR (400 MHz, methanol-$d_3$) δ ppm 8.39 (1 H, br. s.), 7.83 (1 H, s), 7.25-7.38 (2 H, m), 7.07-7.23 (2 H, m), 6.93-7.05 (1 H, m), 6.70 (1 H, d, J=7.9 Hz), 4.64 (1 H, br. s.), 1.30-1.43 (6 H, m).

Preparation 5

(S)-5-(2-(9H-Purin-8-yl)propan-2-yl)-2-chloro-9-fluoro-5H-chromeno[2,3-b]pyridine

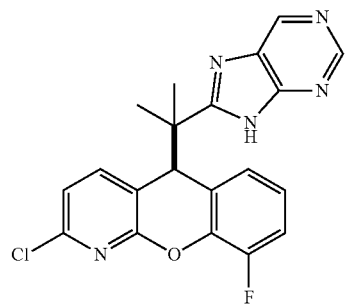 [SMILES: CC(C)(c1nc2cncnc2[nH]1)[C@@H]1c2ccc(Cl)nc2Oc2c(F)cccc21]

Step 1: To a solution of (S)-2-(2-chloro-9-fluoro-5H-chromeno[2,3-b]pyridin-5-yl)-2-methylpropanoyl fluoride (200 mg, 0.618 mmol) in DMF was added pyridine (0.100 mL, 1.236 mmol), pyrimidine-4,5-diamine (102 mg, 0.927 mmol). The reaction mixture was stirred at 80° C. for 32 h. The reaction mixture was then diluted with AcOEt (60 mL), washed with saturated NaHCO$_3$ (2×30 mL), brine, dried over (Na$_2$SO$_4$), and concentrated to dryness and used for next step without further purification. LC-MS, 414 (M+1).

Step 2: The solution of the above intermediate, (S)-N-(5-aminopyrimidin-4-yl)-2-(2-chloro-9-fluoro-5H-chromeno [2,3-b]pyridin-5-yl)-2-methylpropanamide (210 mg, 0.507 mmol), in AcOH was stirred at 90° C. for 16 h. The reaction mixture was cooled, and diluted with AcOEt (60 mL), water (20 mL), and adjusted the pH to basic with Na$_2$CO$_3$. The organic layer was collected, washed with saturated NaHCO$_3$ (2×30 mL), dried over (Na$_2$SO$_4$), and concentrated to dryness and used for next step without further purification. LC-MS, 396 (M+1). HPLC: Rt=2.70 min. Method 2 Column: CHROMOLITH® SpeedROD 4.6×50 mm; Solvent A=10% MeOH–90% H$_2$O, 0.2% H$_3$PO$_4$; Solvent B=90% MeOH–10% H$_2$O, 0.2% H$_3$PO$_4$; 0% B to 100% B over 4 min with 1 min hold. $^1$H NMR (400 MHz, methanol-d$_3$) δ ppm 8.88 (2 H, d, J=10.1 Hz), 7.30-7.38 (1 H, m), 7.08-7.23 (2 H, m), 7.00 (1 H, td, J=8.0, 5.1 Hz), 6.72 (1 H, d, J=7.9 Hz), 4.63 (1 H, s), 1.37 (6 H, d, J=9.2 Hz).

Preparation 6

(S)-2-(9-Fluoro-2-(4-(morpholine-4-carbonyl)phenyl)-5H-chromeno[2,3-b]pyridin-5-yl)-2-methylpropanoic acid

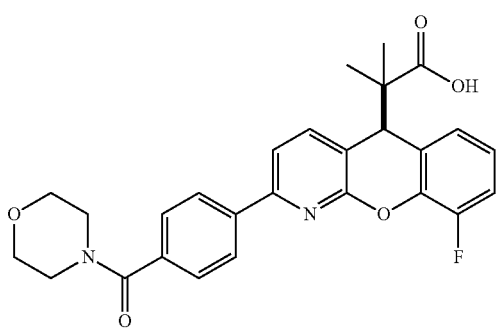 [SMILES: CC(C)(C(=O)O)[C@@H]1c2ccc(-c3ccc(C(=O)N4CCOCC4)cc3)nc2Oc2c(F)cccc21]

To a solution of (S)-2-(2-chloro-9-fluoro-5H-chromeno [2,3-b]pyridin-5-yl)-2-methylpropanoic acid (1.0 g, 3.11 mmol) in DMF (30 mL) was added morpholino(4-(4,4,5,5-tetramethyl-1,3,2-dioxaborolan-2-yl)phenyl)methanone (1.775 g, 5.59 mmol), potassium phosphate (10.88 mL, 21.76 mmol), flushed with N$_2$ for 5 min, and then added tetrakis(triphenylphosphine)palladium (0) (0.359 g, 0.311 mmol). The mixture was stirred at 100° C. for 3 h. After cooling, the mixture was added water (50 mL) and diethyl ether (100 mL), shaken, filtered and separated. The aqueous layer was extracted with ether twice (2×80 mL). The ethereal layer was washed with water (40 mL). The combined aqueous layer was adjusted to acidic (pH=5-6) with conc. HCl and then extracted with AcOEt (100 ml, 50 mL) which was washed with saturated NH$_4$Cl (50 mL), dried over (Na$_2$SO$_4$), and concentrated under vacuo. The residue was re-crystallized with AcOEt and hexane. LC-MS, 477 (M+1). HPLC: Rt=3.65 min. Method 1 Column:YMC S5 ODS-A 4.6×50 mm; Solvent A=10% MeOH–90% H$_2$O, 0.2% H$_3$PO$_4$; Solvent B=90% MeOH–10% H$_2$O, 0.2% H$_3$PO$_4$; 0% B to 100% B over 4 min with 1 min hold. $^1$H NMR (500 MHz, methanol-d$_3$) δ ppm 8.15 (2 H, d, J=8.5 Hz), 7.91 (1 H, d, J=8.0 Hz), 7.78 (1 H, d, J=7.7 Hz), 7.55 (2 H, d, J=8.5 Hz), 7.11-7.25 (3 H, m), 4.55 (1 H, s), 3.42-3.87 (8 H, m), 1.02 (6 H, d, J=14.0 Hz).

Preparation 7

4-(1-Methyl-1H-tetrazol-5-yl)phenylboronic acid

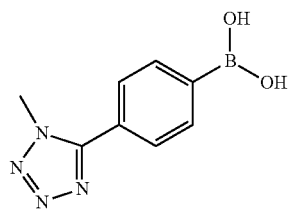

To a solution of N-methyl-4-(4,4,5,5-tetramethyl-1,3,2-dioxaborolan-2-yl)benzamide (150 mg, 0.574 mmol) in MeCN was added sodium azide (112 mg, 1.723 mmol), and the mixture was cooled to 0° C. followed by trifluoromethanesulfonic anhydride (243 mg, 0.862 mmol). The reaction mixture was warmed to r.t slowly and stirred at r.t for o/n. LC-MS indicated that the MS of major peak is identical to the corresponding boronic acid. The mixture was taken into AcOEt (40 mL), washed with saturated NH$_4$Cl (2×20 mL), dried and concentrated under vacuo to give the above title compound which was used for the next as is. LC-MS, 205 (M+1). $^1$H NMR (400 MHz, chloroform-d) δ ppm 7.99 (2 H, d, J=8.1 Hz), 7.68-7.77 (2 H, m), 4.18 (3 H, s).

Preparation 8

(S)-2-(9-Fluoro-2-(4-(1-methyl-1H-tetrazol-5-yl) phenyl)-5H-chromeno[2,3-b]pyridin-5-yl)-2-methylpropanoic acid

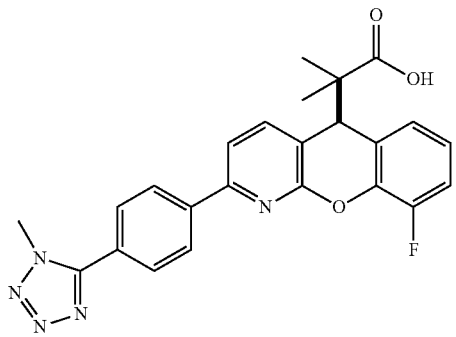 [SMILES: Cn1nnnc1-c1ccc(-c2ccc3c(n2)Oc2c(F)cccc2[C@@H]3C(C)(C)C(=O)O)cc1]

To a solution of (S)-2-(2-chloro-9-fluoro-5H-chromeno [2,3-b]pyridin-5-yl)-2-methylpropanoic acid (200 mg, 0.622 mmol) in DMF was added 4-(1-methyl-1H-tetrazol-5-yl) phenylboronic acid (190 mg, 0.932 mmol), K$_3$PO$_4$ (1.243 mL, 2.487 mmol), and tetrakis (50.3 mg, 0.044 mmol). The mixture was flushed with N$_2$ for 5 min and then stirred at 95° C. for o/n. After cooling, the mixture was filtered and the filtrate was washed with diethyl ether (3×20 mL) and the mother liquor was acidified with 1N HCl to PH=5-6 and extracted with AcOEt (2×30 mL). The organic layer was collected, washed with saturated NH₄Cl (3×20 mL), dried and concentrated under vacuo to get the crude above title compound which was used as is. LC-MS, 446 (M+1). ¹H NMR (400 MHz, chloroform-d) δ ppm 8.25-8.32 (2 H, m), 7.76-7.92 (3 H, m), 7.68 (1 H, d, J=7.7 Hz), 7.04-7.19 (3 H, m), 4.53 (1 H, s), 4.23 (3 H, s), 1.07-1.18 (6 H, m).

Preparation 9

6-(Morpholine-4-carbonyl)pyridin-3-ylboronic acid

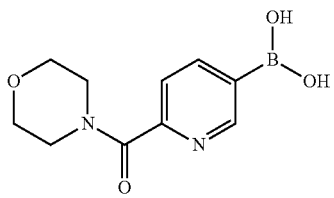 [SMILES: O=C(c1ccc(B(O)O)cn1)N1CCOCC1]

To a solution of 6-(methoxycarbonyl)pyridin-3-ylboronic acid (200 mg, 1.105 mmol) in MeCN was added morpholine (1 mL, 11.48 mmol). The mixture was stirred at 85° C. for o/n, LC-MS indicated no desired product. The solvent was removed and the residue was heated at 120° C. for 5 h. LC-MS indicated that the starting material was gone. The mixture was concentrated under vacuo and the residue was used to next step without further purification. LC-MS, 237 (M+1).

Example 1

(S)-(4-(5-(2-(1H-Imidazo[4,5-b]pyrazin-2-yl)propan-2-yl)-9-fluoro-5H-chromeno[2,3-b]pyridin-2-yl)phenyl)(morpholino)methanone

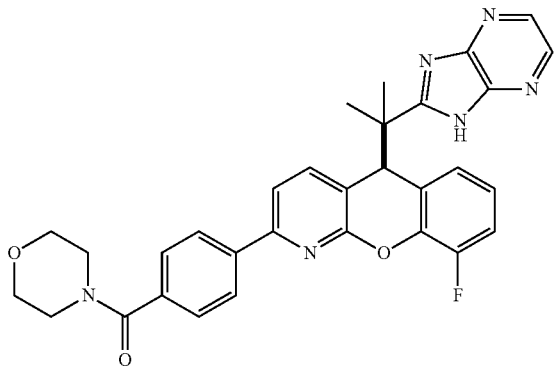 [SMILES: CC(C)(c1nc2nccnc2[nH]1)[C@@H]1c2ccc(-c3ccc(C(=O)N4CCOCC4)cc3)nc2Oc2c(F)cccc21]

To a solution of (S)-5-(2-(1H-imidazo[4,5-b]pyrazin-2-yl)propan-2-yl)-2-chloro-9-fluoro-5H-chromeno[2,3-b]pyridine-derived from Preparation 3 (40 mg, 0.101 mmol) in DMF was added morpholino (4-(4,4,5,5-tetramethyl-1,3,2-dioxaborolan-2-yl)phenyl)methanone (32.1 mg, 0.101 mmol), aqueous K₃PO₄ (0.354 mL, 0.707 mmol). The mixture was flushed with N₂ for 5 min and added tetrakis (11.68 mg, 10.11 μmol). The mixture was flushed again with N₂ for 5 min then stirred at 95° C. for 3 h. After cooling, the mixture was added water (20 mL), extracted with diethyl ether (3×30 mL), the aqueous layer was then collected, extracted with AcOEt (3×40 mL) which was washed with saturated NaHCO₃ (2×30 mL), dried over (Na₂SO₄) and concentrated under vacuo to give the crude product which was purified with prep HPLC to the above title compound as a white solid (TFA salt). LC-MS, 551 (M+1). HPLC, Rt=7.40 min. Method 3 Column:SunFire C18 (150×4.6 mm) 3.5μ; Solvent A=0.05% TFA in H₂O:MeCN (95:5); Solvent B=0.05% TFA in H₂O:MeCN (5:95); 10% B to 100% B over 12 min with 3 min hold. ¹H NMR (400 MHz, methanol-d₃) δ ppm 8.30 (2 H, s), 8.04 (2H, d, J=8.3 Hz), 7.54 (1 H, d, J=7.9 Hz), 7.45 (1 H, d, J=8.3 Hz), 7.37 (1 H, d, J=7.9 Hz), 7.05-7.15 (1 H, m), 6.89 (1 H, td, J=7.9, 4.8 Hz), 6.66 (1 H, d, J=7.9 Hz), 4.59 (1 H, s), 3.32-3.79 (6 H, m), 1.32 (6 H, d, J=6.6 Hz).

Example 2

(S)-1-(4-(5-(2-(1H-Imidazo[4,5-b]pyrazin-2-yl)propan-2-yl)-9-fluoro-5H-chromeno[2,3-b]pyridin-2-yl)phenyl)ethanone

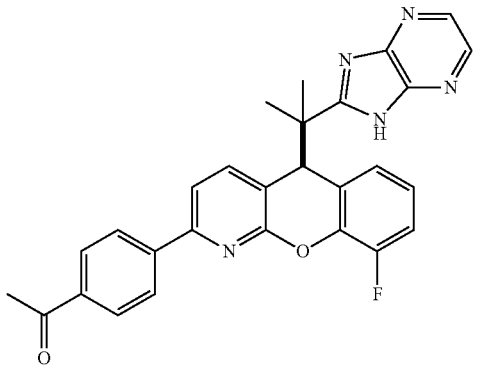 [SMILES: CC(=O)c1ccc(-c2ccc3c(n2)Oc2c(F)cccc2[C@@H]3C(C)(C)c2nc3nccnc3[nH]2)cc1]

Using the procedure described for Example 1 by reaction of 4-acetylphenylboronic acid with the title compound-derived from Preparation 3, the above-title compound was obtained as a white solid. LC-MS, 480 (M+1). HPLC: Rt=3.54 min. Method 2 Column: CHROMOLITH® Speed-ROD 4.6×50 mm; Solvent A=10% MeOH–90% H₂O, 0.2% H₃PO₄; Solvent B=90% MeOH–10% H₂O, 0.2% H₃PO₄; 0% B to 100% B over 4 min with 1 min hold. ¹H NMR (400 MHz, methanol-d₃) δ ppm 8.31 (2 H, s), 8.04-8.10 (2 H, m), 7.97-8.04 (2 H, m), 7.59 (1 H, d, J=7.9 Hz), 7.39 (1 H, d, J=7.9 Hz), 7.04-7.16 (1 H, m), 6.90 (1 H, td, J=8.1, 4.8 Hz), 6.66 (1 H, d, J=7.9 Hz), 4.59 (1 H, s), 2.55 (3 H, s), 1.33 (6 H, d, J=6.2 Hz).

Example 3

(S)-2-(4-(5-(2-(1H-Imidazo[4,5-b]pyrazin-2-yl)propan-2-yl)-9-fluoro-5H-chromeno[2,3-b]pyridin-2-yl)phenyl)propan-2-ol

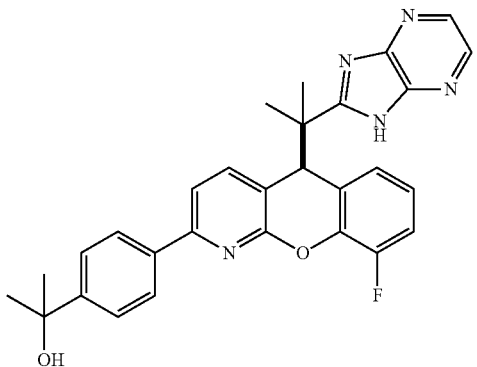 [SMILES: CC(C)(O)c1ccc(-c2ccc3c(n2)Oc2c(F)cccc2[C@@H]3C(C)(C)c2nc3nccnc3[nH]2)cc1]

To a solution of (S)-1-(4-(5-(2-(1H-imidazo[4,5-b]pyrazin-2-yl)propan-2-yl)-9-fluoro-5H-chromeno[2,3-b]pyridin-2-yl)phenyl)ethanone-derived from the previous example (25 mg, 0.052 mmol) in THF was added methylmagnesium bromide (0.261 mL, 0.782 mmol) at 0° C. The mixture was stirred at r.t. for o/n. The reaction mixture was quenched with water (3 mL), diluted with AcOEt (50 mL) and saturated NaHCO$_3$ (20 mL). The organic layer was collected and the aqueous layer was extracted with AcOEt (2×30 mL) which was washed with saturated NaHCO$_3$ (30 mL), dried (Na$_2$SO$_4$) and concentrated under vacuo to give the crude product which was purified with prep HPLC to give the above title compound LC-MS, 496 (M+1). HPLC: Rt=7.96 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.32 (2 H, s), 7.82-7.92 (2 H, m), 7.49 (3 H, dd, J=12.5, 8.1 Hz), 7.34 (1 H, d, J=7.9 Hz), 6.99-7.15 (1 H, m), 6.89 (1 H, td, J=8.1, 4.8 Hz), 6.64 (1 H, d, J=7.9 Hz), 4.57 (1 H, s), 1.47 (6 H, s), 1.32 (6 H, d, J=4.0 Hz).

Example 4

(S)-4-(5-(2-(1H-Imidazo[4,5-b]pyrazin-2-yl)propan-2-yl)-9-fluoro-5H-chromeno[2,3-b]pyridin-2-yl)-N,N-dimethylbenzamide

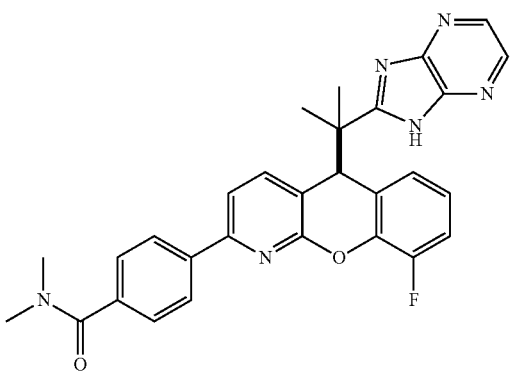 [SMILES: CN(C)C(=O)c1ccc(-c2ccc3c(n2)Oc2c(F)cccc2[C@@H]3C(C)(C)c2nc3nccnc3[nH]2)cc1]

Using the procedure described for Example 1 by reaction of 4-(dimethylcarbamoyl)phenylboronic acid with the title compound-derived from Preparation 3, the above-title compound was obtained as a white solid. LC-MS, 509 (M+1). HPLC: Rt=7.36 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.30 (2 H, s), 8.03 (2 H, d, J=8.3 Hz), 7.54 (1 H, d, J=7.5 Hz), 7.45 (2 H, d, J=8.3 Hz), 7.37 (1 H, d, J=7.9 Hz), 7.09 (1 H, t, J=9.4 Hz), 6.89 (1 H, td, J=7.9, 4.8 Hz), 6.66 (1 H, d, J=7.9 Hz), 4.59 (1 H, s), 3.03 (3 H, s), 2.88-2.99 (3 H, m), 1.26-1.37 (6 H, m), 0.75-0.88 (6 H, m).

Example 5

(S)-5-(2-(1H-Imidazo[4,5-b]pyrazin-2-yl)propan-2-yl)-9-fluoro-2-(4-(methylsulfonyl)phenyl)-5H-chromeno[2,3-b]pyridine

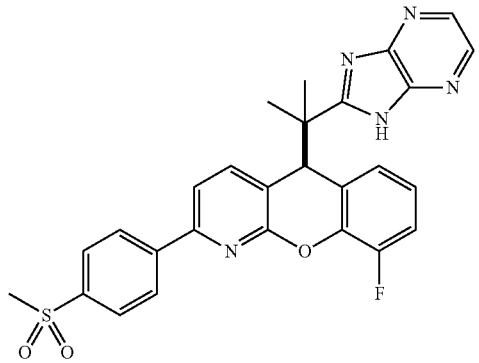

Using the procedure described for Example 1 by reaction of 4-(methylsulfonyl)phenylboronic acid with the title compound-derived from Preparation 3, the above-title compound was obtained as a white solid. LC-MS, 516 (M+1). HPLC: Rt=7.85 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.31 (2H, s), 8.20 (2 H, d, J=8.8 Hz), 7.96 (2 H, d, J=8.8 Hz), 7.62 (1 H, d, J=7.9 Hz), 7.42 (1 H, d, J=7.9 Hz), 7.04-7.18 (1 H, m), 6.91 (1 H, td, J=8.0, 5.1 Hz), 6.67 (1 H, d, J=7.9 Hz), 4.60 (1 H, s), 3.03-3.12 (3 H, m), 1.33 (6 H, d, J=6.2 Hz).

Example 6

(S)-5-(2-(1H-Imidazo[4,5-b]pyrazin-2-yl)propan-2-yl)-2-(4-(ethylsulfonyl)phenyl)-9-fluoro-5H-chromeno[2,3-b]pyridine

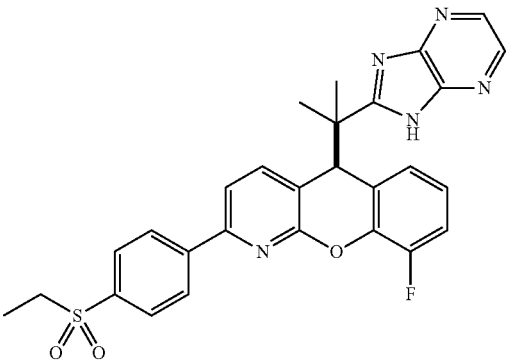

Using the procedure described for Example 1 by reaction of 4-(ethylsulfonyl)phenylboronic acid with the title compound-derived from Preparation 3, the above-title compound was obtained as a white solid. LC-MS, 530 (M+1). HPLC: Rt=3.37 min. Method 2 Column: CHROMOLITH® SpeedROD 4.6×50 mm; Solvent A=10% MeOH–90% H$_2$O, 0.2% H$_3$PO$_4$; Solvent B=90% MeOH–10% H$_2$O, 0.2%

H₃PO₄; 0% B to 100% B over 4 min with 1 min hold. ¹H NMR (400 MHz, methanol-d₃) δ ppm 8.41 (2 H, s), 8.25-8.36 (2 H, m), 7.96-8.05 (2 H, m), 7.72 (1 H, d, J=7.5 Hz), 7.52 (1 H, d, J=7.5 Hz), 7.18 (1 H, d, J=8.3 Hz), 6.95-7.05 (1 H, m), 6.77 (1 H, d, J=7.9 Hz), 4.69 (1 H, s), 3.12-3.26 (2 H, m), 1.42 (6 H, d, J=4.8 Hz), 1.17-1.31 (3 H, m).

Example 7

(S)-5-(2-(1H-Imidazo[4,5-b]pyrazin-2-yl)propan-2-yl)-9-fluoro-2-(4-(isopropylsulfonyl)phenyl)-5H-chromeno[2,3-b]pyridine

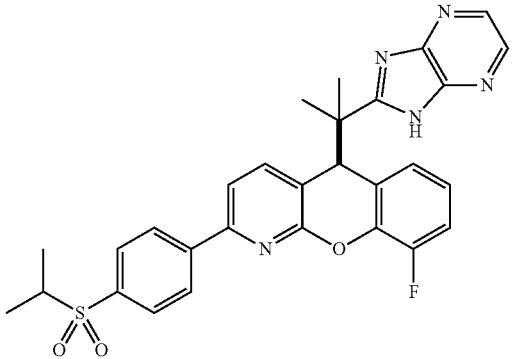 [SMILES: CC(C)S(=O)(=O)c1ccc(-c2ccc3c(n2)Oc2c(F)cccc2[C@@H]3C(C)(C)c2nc3nccnc3[nH]2)cc1]

Using the procedure described for Example 1 by reaction of 4-(isopropylsulfonyl)phenylboronic acid with the title compound-derived from Preparation 3, the above-title compound was obtained as a white solid. LC-MS, 544 (M+1). HPLC: Rt=3.46 min. Method 2 Column: CHROMOLITH® SpeedROD 4.6×50 mm; Solvent A=10% MeOH–90% H₂O, 0.2% H₃PO₄; Solvent B=90% MeOH–10% H₂O, 0.2% H₃PO₄; 0% B to 100% B over 4 min with 1 min hold. ¹H NMR (400 MHz, methanol-d₃) δ ppm 8.39 (2 H, s), 8.31 (2 H, d, J=8.3 Hz), 7.99 (2 H, d, J=8.3 Hz), 7.72 (1 H, d, J=7.9 Hz), 7.51 (1 H, d, J=7.9 Hz), 7.19 (1 H, t, J=8.8 Hz), 7.00 (1 H, td, J=8.1, 4.8 Hz), 6.77 (1 H, d, J=7.9 Hz), 4.70 (1 H, s), 3.34-3.42 (1 H, m), 1.42 (6 H, d, J=6.6 Hz), 1.24-1.32 (6 H, m).

Example 8

(S)-5-(2-(1H-Imidazo[4,5-b]pyrazin-2-yl)propan-2-yl)-9-fluoro-2-(4-isopropoxyphenyl)-5H-chromeno[2,3-b]pyridine

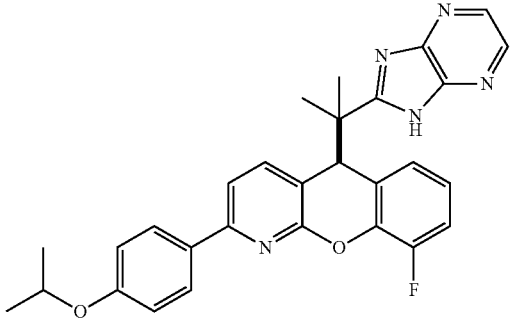 [SMILES: CC(C)Oc1ccc(-c2ccc3c(n2)Oc2c(F)cccc2[C@@H]3C(C)(C)c2nc3nccnc3[nH]2)cc1]

Using the procedure described for Example 1 by reaction of 4-isopropoxyphenylboronic acid with the title compound-derived from Preparation 3, the above-title compound was obtained as a white solid. LC-MS, 496 (M+1). HPLC: Rt=9.84 min. Method 3 Column: SunFire C18 (150×4.6 mm) 3.5μ; Solvent A=0.05% TFA in H₂O:MeCN (95:5); Solvent B=0.05% TFA in H₂O:MeCN (5:95); 10% B to 100% B over 12 min with 3 min hold. ¹H NMR (400 MHz, methanol-d₃) δ ppm 8.31 (2 H, s), 7.78-7.89 (2 H, m), 7.39 (1 H, d, J=7.9 Hz), 7.29 (1 H, d, J=7.9 Hz), 7.04-7.14 (1 H, m), 6.84-6.94 (3 H, m), 6.62 (1 H, d, J=7.9 Hz), 4.57-4.63 (1 H, m), 4.53-4.57 (1 H, m), 1.31 (6 H, d, J=3.5 Hz), 1.22-1.27 (6 H, m).

Example 9

(S)-5-(2-(1H-Imidazo[4,5-b]pyrazin-2-yl)propan-2-yl)-2-(3-chloro-4-isopropoxyphenyl)-9-fluoro-5H-chromeno[2,3-b]pyridine

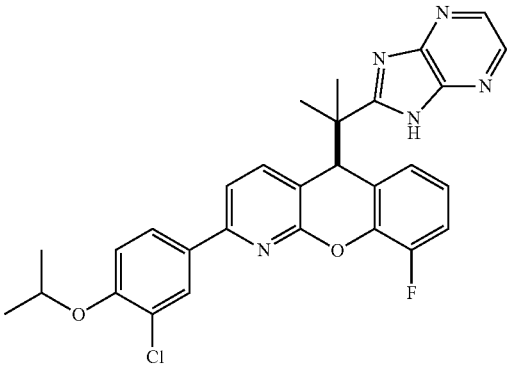 [SMILES: CC(C)Oc1ccc(-c2ccc3c(n2)Oc2c(F)cccc2[C@@H]3C(C)(C)c2nc3nccnc3[nH]2)cc1Cl]

Using the procedure described for Example 1 by reaction of 3-chloro-4-isopropoxyphenylboronic acid with the title compound-derived from Preparation 3, the above-title compound was obtained as a white solid. LC-MS, 530 (M+1). HPLC: Rt=10.50 min. Method 3 Column: SunFire C18 (150×4.6 mm) 3.5μ; Solvent A=0.05% TFA in H₂O:MeCN (95:5); Solvent B=0.05% TFA in H₂O:MeCN (5:95); 10% B to 100% B over 12 min with 3 min hold. ¹H NMR (400 MHz, methanol-d₃) δ ppm 8.40 (2 H, s), 8.07 (1 H, d, J=2.2 Hz), 7.91 (1 H, dd, J=8.8, 2.2 Hz), 7.52 (1 H, d, J=7.9 Hz), 7.40 (1 H, d, J=7.9 Hz), 7.11-7.22 (2 H, m), 6.97 (1 H, td, J=8.1, 4.8 Hz), 6.72 (1 H, d, J=7.9 Hz), 4.69-4.76 (1 H, m), 4.65 (1 H, s), 1.29-1.46 (12 H, m).

Example 10

(S)-5-(2-(1H-Imidazo[4,5-b]pyrazin-2-yl)propan-2-yl)-9-fluoro-2-(3-fluoro-4-isopropoxyphenyl)-5H-chromeno[2,3-b]pyridine

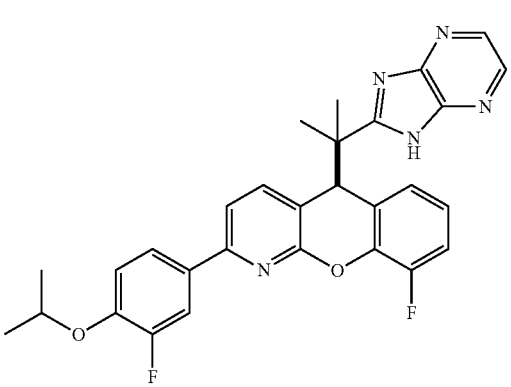 [SMILES: CC(C)Oc1ccc(-c2ccc3c(n2)Oc2c(F)cccc2[C@@H]3C(C)(C)c2nc3nccnc3[nH]2)cc1F]

Using the procedure described for Example 1 by reaction of 2-(3-fluoro-4-isopropoxyphenyl)-4,4,5,5-tetramethyl-1,3,2-dioxaborolane with the title compound-derived from Preparation 3, the above-title compound was obtained as a white solid. LC-MS, 514 (M+1). HPLC: Rt=9.90 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.40 (2 H, s), 7.73-7.87 (2 H, m), 7.52 (1 H, d, J=7.9 Hz), 7.40 (1 H, d, J=7.9 Hz), 7.11-7.25 (2 H, m), 6.97 (1 H, td, J=7.9, 4.8 Hz), 6.72 (1 H, d, J=7.9 Hz), 4.67-4.74 (1 H, m), 4.62-4.67 (1 H, m), 1.32-1.47 (12 H, m).

Example 11

(S)-5-(2-(1H-Imidazo[4,5-b]pyrazin-2-yl)propan-2-yl)-2-(4-tert-butoxyphenyl)-9-fluoro-5H-chromeno[2,3-b]pyridine

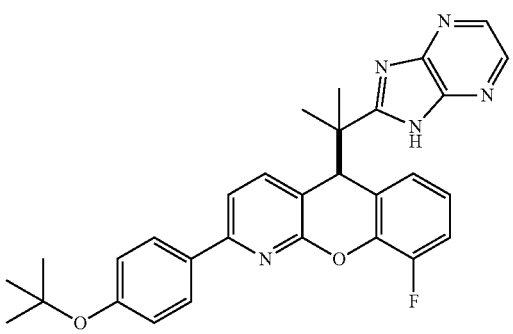 [SMILES: CC(C)(C)Oc1ccc(-c2ccc3c(n2)Oc2c(F)cccc2[C@@H]3C(C)(C)c2nc3nccnc3[nH]2)cc1]

Using the procedure described for Example 1 by reaction of 4-tert-butoxyphenylboronic acid with the title compound-derived from Preparation 3, the above-title compound was obtained as a white solid. LC-MS, 510 (M+1). HPLC: Rt=9.96 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, chloroform-d) δ ppm 8.43 (1 H, br. s.), 7.85-7.94 (2 H, m), 7.29-7.36 (2 H, m), 6.99-7.10 (3 H, m), 6.84 (1 H, td, J=7.9, 4.8 Hz), 6.63 (1 H, d, J=7.5 Hz), 4.81 (1 H, s), 1.45 (6 H, s), 1.31-1.42 (9 H, m).

Example 12

(S)-5-(2-(1H-Imidazo[4,5-b]pyrazin-2-yl)propan-2-yl)-2-(4-ethoxyphenyl)-9-fluoro-5H-chromeno[2,3-b]pyridine

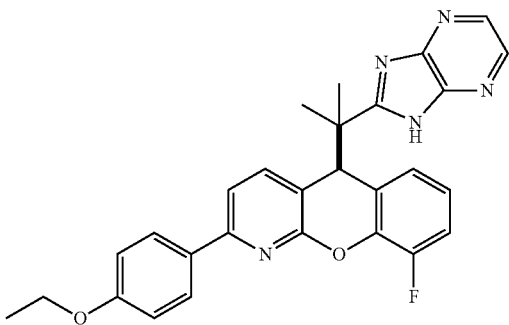 [SMILES: CCOc1ccc(-c2ccc3c(n2)Oc2c(F)cccc2[C@@H]3C(C)(C)c2nc3nccnc3[nH]2)cc1]

Using the procedure described for Example 1 by reaction of 4-ethoxyphenylboronic acid with the title compound-derived from Preparation 3, the above-title compound was obtained as a white solid. LC-MS, 482 (M+1). HPLC: Rt=9.45 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.40 (2 H, s), 7.94 (2H, d, J=9.2 Hz), 7.45-7.53 (1 H, m), 7.38 (1 H, d, J=7.9 Hz), 7.16 (1 H, d, J=10.5 Hz), 6.92-7.05 (3 H, m), 6.71 (1 H, s), 4.64 (1 H, s), 4.10 (2 H, q, J=6.7 Hz), 1.32-1.49 (9 H, m).

Example 13

(S)-5-(2-(1H-Imidazo[4,5-b]pyrazin-2-yl)propan-2-yl)-9-fluoro-2-(4-(trifluoromethoxy)phenyl)-5H-chromeno[2,3-b]pyridine

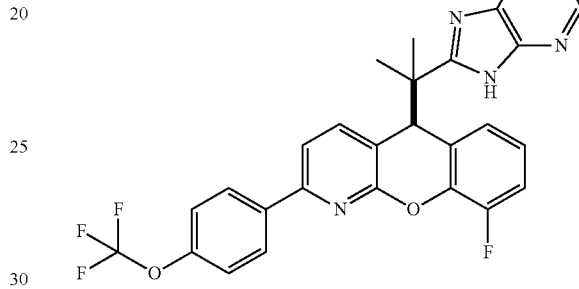

Using the procedure described for Example 1 by reaction of 4-(trifluoromethoxy)phenylboronic acid with the title compound-derived from Preparation 3, the above-title compound was obtained as a white solid. LC-MS, 522 (M+1). HPLC: Rt=10.03 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, MeOD) δ ppm 8.37 (2 H, s), 8.04-8.14 (2 H, m), 7.57 (1 H, d, J=7.9 Hz), 7.42 (1 H, d, J=7.9 Hz), 7.34 (2 H, d, J=8.1 Hz), 7.10-7.19 (1 H, m), 6.95 (1 H, td, J=8.0, 5.0 Hz), 6.70 (1 H, d, J=7.9 Hz), 4.63 (1 H, s), 1.37 (6 H, d, J=4.4 Hz).

Example 14

(S)-(4-(5-(2-(1H-Benzo[d]imidazol-2-yl)propan-2-yl)-9-fluoro-5H-chromeno[2,3-b]pyridin-2-yl)phenyl)(morpholino)methanone

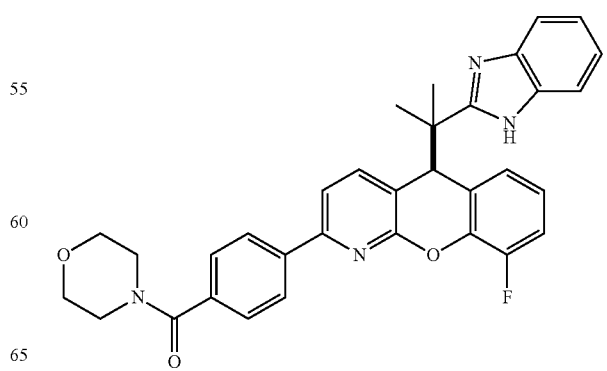

Step 1: To a solution of (S)-2-(9-fluoro-2-(4-(morpholine-4-carbonyl)phenyl)-5H-chromeno[2,3-b]pyridin-5-yl)-2-methylpropanoic acid-derived from the preparation 6 (65 mg, 0.136 mmol) in DMF (5 mL) was added benzene-1,2-diamine (73.8 mg, 0.682 mmol), DIEA (95 μL, 0.546 mmol), EDC (78 mg, 0.409 mmol), HOBt (62.7 mg, 0.409 mmol), and stirred at rt for 2 days. The reaction mixture was diluted with water, extracted with EtOAc. The organic layer was collected and concentrated on the ROTAVAPOR® to give the crude product. LC-MS, 522 (M+1).

Step 2: The intermediate which was prepared from the previous step was dissolved in AcOH (4 mL) and stirred at 75° C. for 16 h. The crude material was purified on a prep HPLC to give the above title compound as a TFA salt. LC-MS, 549 (M+1). HPLC: PHENOMENEX® Luna 5 g 21.2×100 mm: The product was collect at the RT=16.52-16.68 min. Start % B=10, Final % B=100, Gradient Time=20 min, Stop Time=20 min, Flow rate=10 ml/min, Wavelength=220, Solvent A=10% MeOH–90% H$_2$O–0.1% TFA, Solvent B=90% MeOH–10% H$_2$O–0.1% TFA. $^1$H NMR (400 MHz, methanol-d$_3$) δ ppm 8.17 (1 H, d, J=8.79 Hz), 7.52-7.88 (8 H, m), 7.27 (1 H, t, J=8.79 Hz), 7.11 (1 H, td, J=8.13, 4.83 Hz), 6.84 (1 H, d, J=7.91 Hz), 4.63 (1 H, s), 3.42-3.93 (8 H, m), 1.59 (6 H, d, J=16.70 Hz).

Example 15

(S)-(4-(5-(2-(3H-Imidazo[4,5-b]pyridin-2-yl)propan-2-yl)-9-fluoro-5H-chromeno[2,3-b]pyridin-2-yl)phenyl)(morpholino)methanone

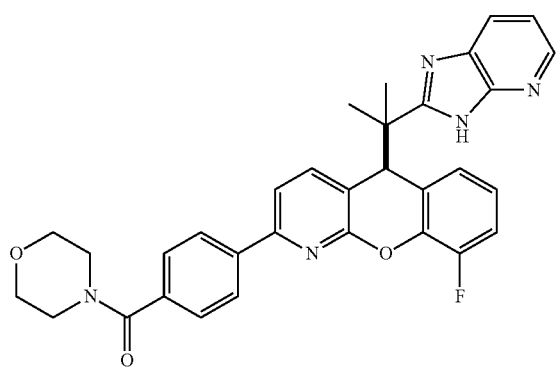 [SMILES: CC(C)(c1nc2cccnc2[nH]1)[C@@H]1c2ccc(-c3ccc(C(=O)N4CCOCC4)cc3)nc2Oc2c(F)cccc21]

Using the procedure described for Example 1 by reaction of morpholino(4-(4,4,5,5-tetramethyl-1,3,2-dioxaborolan-2-yl)phenyl)methanone with the title compound-derived from Preparation 4, the above-title compound was obtained as a white solid. LC-MS, 550 (M+1). HPLC: Rt=7.22 min. Method 3 Column: SunFire C18 (150×4.6 mm) 3.5μ; Solvent A=0.05% TFA in H$_2$O:MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 9.26-9.57 (1 H, m), 8.61 (1 H, br. s.), 8.27 (2 H, br. s.), 7.85-7.98 (2 H, m), 7.58-7.82 (3 H, m), 6.72-7.30 (2 H, m), 6.00-6.58 (1 H, m), 5.09 (1 H, s), 3.44-3.91 (8 H, m), 1.40-1.64 (6 H, m).

Example 16

(S)-(4-(5-(2-(9H-Purin-8-yl)propan-2-yl)-9-fluoro-5H-chromeno[2,3-b]pyridin-2-yl)phenyl)(morpholino)methanone

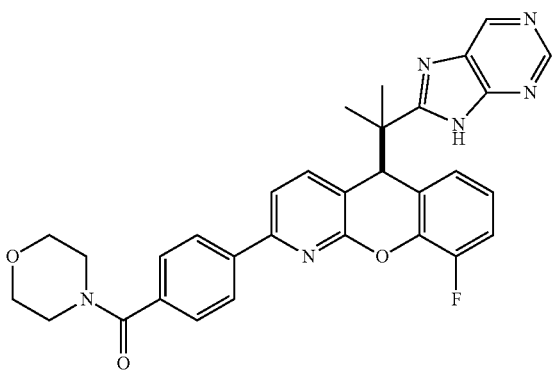 [SMILES: CC(C)(c1nc2cncnc2[nH]1)[C@@H]1c2ccc(-c3ccc(C(=O)N4CCOCC4)cc3)nc2Oc2c(F)cccc21]

Using the procedure described for Example 1 by reaction of morpholino(4-(4,4,5,5-tetramethyl-1,3,2-dioxaborolan-2-yl)phenyl)methanone with the title compound-derived from Preparation 5, the above-title compound was obtained as a white solid. LC-MS, 551 (M+1). HPLC: Rt=6.53 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.96 (2 H, d, J=14.1 Hz), 8.04 (2 H, d, J=8.3 Hz), 7.58 (1 H, d, J=7.9 Hz), 7.38-7.52 (3 H, m), 7.05-7.16 (1 H, m), 6.93 (1 H, td, J=7.9, 4.8 Hz), 6.68 (1 H, d, J=7.9 Hz), 4.56 (1 H, s), 3.32-3.76 (8 H, m), 1.36 (6 H, s).

Example 17

(S)-5-(2-(9H-Purin-8-yl)propan-2-yl)-9-fluoro-2-(4-(methylsulfonyl)phenyl)-5H-chromeno[2,3-b]pyridine

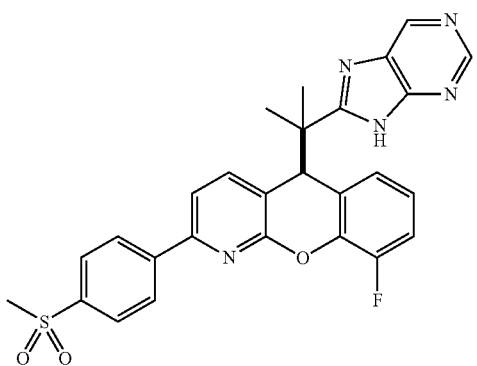 [SMILES: CC(C)(c1nc2cncnc2[nH]1)[C@@H]1c2ccc(-c3ccc(S(C)(=O)=O)cc3)nc2Oc2c(F)cccc21]

Using the procedure described for Example 1 by reaction of 4-(methylsulfonyl)phenylboronic acid with the title compound-derived from Preparation 5, the above-title compound was obtained as a white solid. LC-MS, 516 (M+1). HPLC: Rt=7.09 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, methanol-$d_3$) δ ppm 8.97 (2H, d, J=14.9 Hz), 8.20 (2 H, d, J=8.8 Hz), 7.96 (2 H, d, J=8.8 Hz), 7.65 (1 H, d, J=7.5 Hz), 7.47 (1 H, d, J=7.9 Hz), 7.05-7.19 (1 H, m), 6.94 (1 H, td, J=8.1, 4.8 Hz), 6.69 (1H, d, J=7.5 Hz), 4.57 (1 H, s), 3.01-3.11 (3 H, m), 1.29-1.40 (6 H, m).

Example 18

(S)-5-(2-(1H-Imidazo[4,5-b]pyrazin-2-yl)propan-2-yl)-9-fluoro-2-(4-morpholinophenyl)-5H-chromeno[2,3-b]pyridine

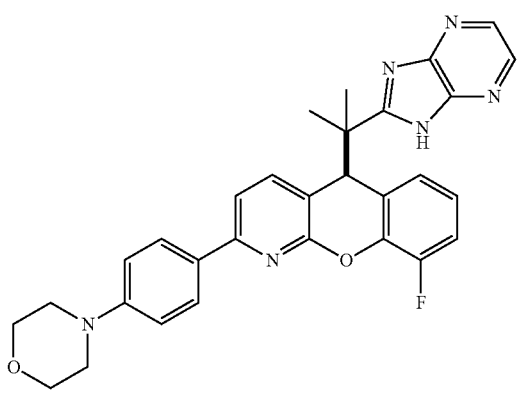 [SMILES: CC(C)(c1nc2nccnc2[nH]1)[C@@H]1c2ccc(-c3ccc(N4CCOCC4)cc3)nc2Oc2c(F)cccc21]

Using the procedure described for Example 1 by reaction of 4-morpholinophenylboronic acid with the title compound-derived from Preparation 3, the above-title compound was obtained as a white solid. LC-MS, 523 (M+1). HPLC: Rt=8.59 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, methanol-$d_3$) δ ppm 8.57 (2 H, br. s.), 8.26 (2 H, d, J=8.8 Hz), 7.78 (2 H, br. s.), 7.15 (3 H, d, J=8.3 Hz), 6.90 (1 H, br. s.), 5.97-6.55 (1 H, m), 4.95-5.03 (1 H, m), 3.81-3.93 (4 H, m), 1.40-1.63 (6 H, m).

Example 19

(S)-N-(4-(5-(2-(1H-Imidazo[4,5-b]pyrazin-2-yl)propan-2-yl)-9-fluoro-5H-chromeno[2,3-b]pyridin-2-yl)phenyl)acetamide

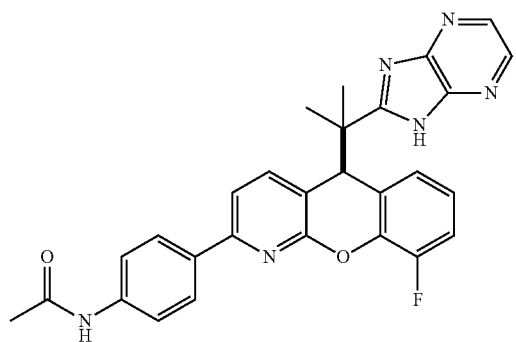 [SMILES: CC(=O)Nc1ccc(-c2ccc3c(n2)Oc2c(F)cccc2[C@@H]3C(C)(C)c2nc3nccnc3[nH]2)cc1]

Using the procedure described for Example 1 by reaction of 4-acetamidophenylboronic acid with the title compound-derived from Preparation 3, the above-title compound was obtained as a white solid. LC-MS, 495 (M+1). HPLC: Rt=7.44 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, MeOD) δ ppm 8.47-8.72 (2 H, m), 8.30 (2 H, d, J=8.8 Hz), 7.84 (2 H, br. s.), 7.48-7.74 (2 H, m), 7.20 (1 H, d, J=8.0 Hz), 6.90 (1 H, br. s.), 5.96-6.52 (1 H, m), 4.96-5.08 (1 H, m), 2.07-2.21 (3 H, m), 1.38-1.60 (6 H, m).

Example 20

(S)-5-(2-(1H-Imidazo[4,5-b]pyrazin-2-yl)propan-2-yl)-9-fluoro-2-phenyl-5H-chromeno[2,3-b]pyridine

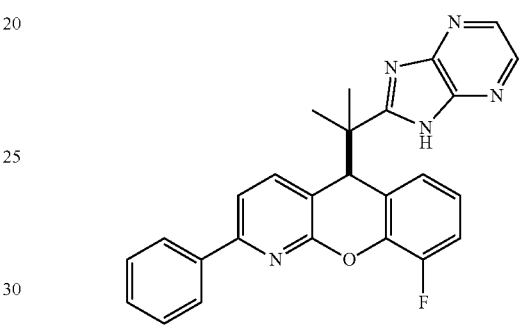

Using the procedure described for Example 1 by reaction of 4,4,5,5-tetramethyl-2-phenyl-1,3,2-dioxaborolane with the title compound-derived from Preparation 3, the above-title compound was obtained as a white solid. LC-MS, 438 (M+1). HPLC: Rt=9.01 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, MeOD) δ ppm 8.31 (2 H, s), 7.86-7.96 (2 H, m), 7.48 (1 H, d, J=7.7 Hz), 7.29-7.42 (4 H, m), 7.02-7.15 (1 H, m), 6.88 (1 H, td, J=8.0, 4.8 Hz), 6.64 (1 H, d, J=7.7 Hz), 4.57 (1 H, s), 1.32 (6 H, d, J=4.0 Hz).

Example 21

(S)-5-(2-(1H-Imidazo[4,5-b]pyrazin-2-yl)propan-2-yl)-9-fluoro-2-(pyridin-4-yl)-5H-chromeno[2,3-b]pyridine

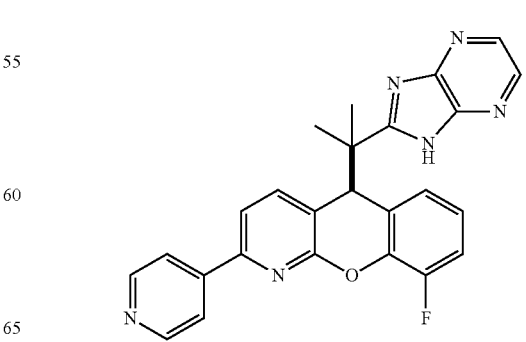

Using the procedure described for Example 1 by reaction of pyridin-4-ylboronic acid with the title compound-derived from Preparation 3, the above-title compound was obtained as a white solid. LC-MS, 439 (M+1). HPLC: Rt=2.52 min. Method 2 Column: CHROMOLITH® SpeedROD 4.6×50 mm; Solvent A=10% MeOH–90% H₂O, 0.2% H₃PO₄; Solvent B=90% MeOH–10% H₂O, 0.2% H₃PO₄; 0% B to 100% B over 4 min with 1 min hold. ¹H NMR (400 MHz, MeOD) δ ppm 8.96-9.05 (1 H, m), 8.92 (2 H, d, J=6.8 Hz), 8.72 (2 H, d, J=6.8 Hz), 8.43 (2 H, s), 8.04 (1 H, d, J=7.7 Hz), 7.70 (1 H, d, J=8.1 Hz), 7.20-7.31 (1 H, m), 7.08 (1 H, td, J=8.0, 4.8 Hz), 6.85 (1 H, d, J=7.9 Hz), 4.77 (1 H, s), 1.46 (6 H, d, J=8.1 Hz).

Example 22

(S)-4-(5-(2-(1H-Imidazo[4,5-b]pyrazin-2-yl)propan-2-yl)-9-fluoro-5H-chromeno[2,3-b]pyridin-2-yl)aniline

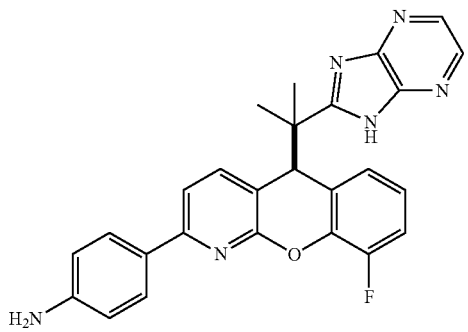 [SMILES: CC(C)(c1nc2nccnc2[nH]1)[C@@H]1c2ccc(-c3ccc(N)cc3)nc2Oc2c(F)cccc21]

Using the procedure described for Example 1 by reaction of 4-(4,4,5,5-tetramethyl-1,3,2-dioxaborolan-2-yl)aniline with the title compound-derived from Preparation 3, the above-title compound was obtained as a white solid. LC-MS, 453 (M+1). HPLC: Rt=5.85 min. Method 3 Column: SunFire C18 (150×4.6 mm) 3.5μ; Solvent A=0.05% TFA in H₂O: MeCN (95:5); Solvent B=0.05% TFA in H₂O:MeCN (5:95); 10% B to 100% B over 12 min with 3 min hold. ¹H NMR (400 MHz, MeOD) δ ppm 8.43 (2 H, s), 8.10-8.20 (2 H, m), 7.63 (1 H, d, J=7.7 Hz), 7.44-7.53 (1 H, m), 7.40 (2 H, d, J=8.8 Hz), 7.18-7.27 (1 H, m), 7.03 (1 H, td, J=8.0, 5.0 Hz), 6.79 (1 H, d, J=7.7 Hz), 4.69 (1 H, s), 1.44 (6 H, d, J=6.8 Hz).

Example 23

(S)-N-(4-(5-(2-(1H-Imidazo[4,5-b]pyrazin-2-yl)propan-2-yl)-9-fluoro-5H-chromeno[2,3-b]pyridin-2-yl)phenyl)methanesulfonamide

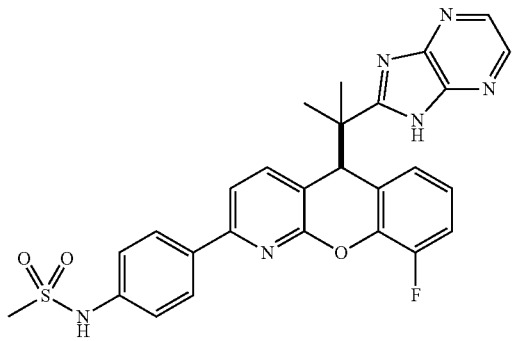 [SMILES: CC(C)(c1nc2nccnc2[nH]1)[C@@H]1c2ccc(-c3ccc(NS(C)(=O)=O)cc3)nc2Oc2c(F)cccc21]

Step 1: To a solution of the title compound-derived from the Example 22, (S)-4-(5-(2-(1H-imidazo[4,5-b]pyrazin-2-yl)propan-2-yl)-9-fluoro-5H-chromeno[2,3-b]pyridin-2-yl)aniline (25 mg, 0.055 mmol), in DCM, was added TEA (0.023 mL, 0.166 mmol), methanesulfonyl chloride (14.56 mg, 0.127 mmol). The mixture was stirred at r.t for 1 h. The reaction mixture was diluted with DCM (40 mL), washed with saturated NaHCO₃ (2×30 mL), dried over (Na₂SO₄), and concentrated under vacuo to give the crude intermediate which was used for the next step without further purification. LC-MS, 609 (M+1).

Step 2: To a solution of the intermediate-derived from the previous step, (S)-N-(4-(9-fluoro-5-(2-(1-(methylsulfonyl)-1H-imidazo[4,5-b]pyrazin-2-yl)propan-2-yl)-5H-chromeno[2,3-b]pyridin-2 yl)phenyl)methanesulfonamide (33.5 mg, 0.055 mmol) in THF was added TBAF (0.083 mL, 0.083 mmol) (1M in THF). The mixture was stirred at r.t for o/n. The reaction mixture was diluted with AcOEt (50 mL), washed with saturated NH₄Cl (2×30 mL), dried over (Na₂SO₄), and concentrated under vacuo to give the crude product which was purified with a prep HPLC to get the above title compound as a TFA salt. LC-MS, 531 (M+1). HPLC: Rt=7.66 min. Method 3 Column: SunFire C18 (150×4.6 mm) 3.5μ; Solvent A=0.05% TFA in H₂O: MeCN (95:5); Solvent B=0.05% TFA in H₂O:MeCN (5:95); 10% B to 100% B over 12 min with 3 min hold. ¹H NMR (400 MHz, MeOD) δ ppm 8.33 (2 H, s), 7.79-7.97 (2 H, m), 7.47 (1 H, d, J=7.7 Hz), 7.34 (1 H, d, J=7.9 Hz), 7.20-7.29 (2 H, m), 7.03-7.12 (1 H, m), 6.89 (1 H, td, J=8.0, 4.8 Hz), 6.65 (1 H, d, J=7.7 Hz), 4.56 (1 H, s), 2.90-2.95 (3 H, m), 1.32 (6 H, d, J=3.1 Hz).

Example 24

(S)-1-(4-(5-(2-(1H-Imidazo[4,5-b]pyrazin-2-yl)propan-2-yl)-9-fluoro-5H-chromeno[2,3-b]pyridin-2-yl)phenyl)pyrrolidin-2-one

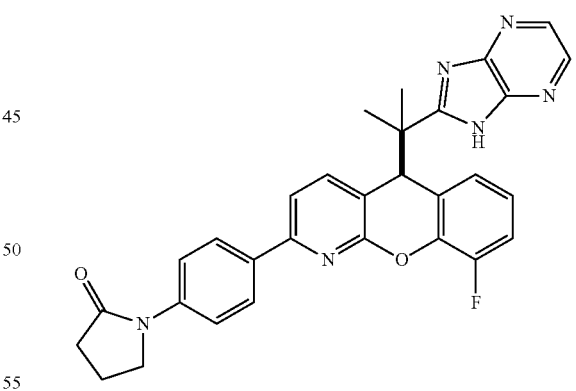

Step 1: To a solution of the title compound-derived from the Example 22, (S)-4-(5-(2-(1H-imidazo[4,5-b]pyrazin-2-yl)propan-2-yl)-9-fluoro-5H-chromeno[2,3-b]pyridin-2-yl)aniline (50 mg, 0.111 mmol), in DMF was added 4-chlorobutanoic acid (13.54 mg, 0.111 mmol), BOP (98 mg, 0.221 mmol), and DIEA (0.058 mL, 0.332 mmol). The mixture was stirred at r.t for 4 h, and then was diluted with AcOEt (40 mL), washed with saturated NaHCO₃ (2×30 mL), dried over (Na₂SO₄), and concentrated under vacuo to give the crude product which was used for the next step without further purification. LC-MS, 558 (M+1).

Step 2: To a solution of the intermediate-derived from the previous step, (S)-N-(4-(5-(2-(1H-imidazo[4,5-b]pyrazin-2-yl)propan-2-yl)-9-fluoro-5H-chromeno[2,3-b]pyridin-2-yl)phenyl)-4-chlorobutanamide (61 mg, 0,110 mmol), in DMF was added K$_2$CO$_3$ (76 mg, 0,548 mmol). The mixture was stirred at 50° C. for o/n. The mixture was diluted with AcOEt (40 mL), washed with saturated NaHCO$_3$ (2×30 mL), dried over (Na$_2$SO$_4$), and concentrated under vacuo to give the crude product which was used for the next step without further purification. LC-MS, 656 (M+1).

Step 3: To a solution of the intermediate-derived from the previous step, 4-(4-((5S)-5-(2-(1-(1H-benzo[d][1,2,3]triazol-1-yl)-1H-imidazo[4,5-b]pyrazin-2-yl)propan-2-yl)-9-fluoro-5H-chromeno[2,3-b]pyridin-2-yl)phenylamino)butanoic acid (50 mg, 0.076 mmol), in THF was added TBAF (0.381 mL, 0.381 mmol) (1M in THF). The mixture was stirred at r.t for o/n and then at 55° C. for 7 h. The mixture was diluted with AcOEt (50 mL), washed with saturated NH$_4$Cl (2×30 mL), dried over (Na$_2$SO$_4$), and concentrated under vacuo. The residue was purified with a prep HPLC to the above title compound as a TFA salt. LC-MS, 521 (M+1). HPLC: Rt=6.76 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.40 (2 H, s), 8.05 (2 H, d, J=8.8 Hz), 7.76 (2 H, d, J=8.8 Hz), 7.57 (1 H, d, J=7.9 Hz), 7.42 (1 H, d, J=7.9 Hz), 7.14-7.24 (1 H, m), 6.98 (1 H, td, J=8.0, 5.1 Hz), 6.73 (1 H, d, J=7.9 Hz), 4.65 (1 H, s), 3.98 (2 H, t, J=7.3 Hz), 2.62 (2 H, t, J=8.1 Hz), 2.20 (2 H, qd, J=7.6, 7.5 Hz), 1.31-1.47 (6 H, m).

Example 25

(S)-5-(2-(1H-Imidazo[4,5-b]pyrazin-2-yl)propan-2-yl)-9-fluoro-2-(6-isopropoxypyridin-3-yl)-5H-chromeno[2,3-b]pyridine

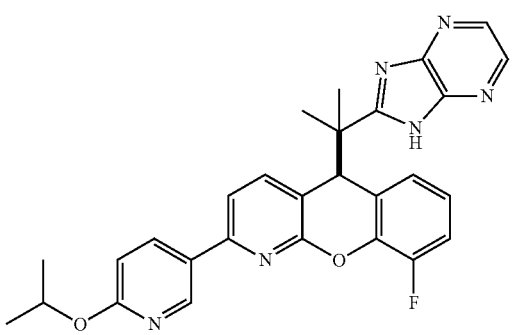

Using the procedure described for Example 1 by reaction of 2-isopropoxy-5-(4,4,5,5-tetramethyl-1,3,2-dioxaborolan-2-yl)pyridine with the title compound-derived from Preparation 3, the above-title compound was obtained as a white solid. LC-MS, 497 (M+1). HPLC: Rt=8.89 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 8.79 (1 H, d, J=2.2 Hz), 8.29-8.47 (3 H, m), 7.57 (1 H, d, J=7.9 Hz), 7.46 (1 H, d, J=7.9 Hz), 7.10-7.28 (1 H, m), 6.87-7.05 (2 H, m), 6.75 (1 H, d, J=7.9 Hz), 5.30 (1 H, dt, J=12.3, 6.2 Hz), 4.66 (1 H, s), 1.32-1.47 (12 H, m).

Example 26

(S)-Methyl 5-(5-(2-(1H-imidazo[4,5-b]pyrazin-2-yl)propan-2-yl)-9-fluoro-5H-chromeno[2,3-b]pyridin-2-yl)picolinate

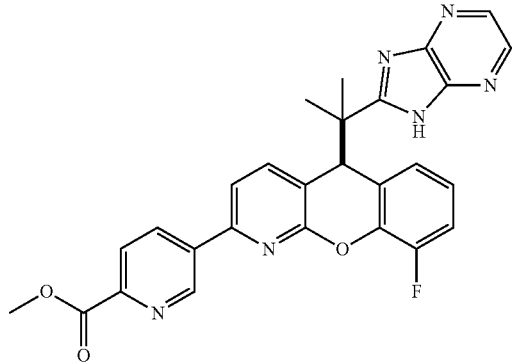 [SMILES: COC(=O)c1ccc(-c2ccc3c(n2)Oc2c(F)cccc2[C@@H]3C(C)(C)c2nc3nccnc3[nH]2)cn1]

Using the procedure described for Example 1 by reaction of methyl 5-(4,4,5,5-tetramethyl-1,3,2-dioxaborolan-2-yl)picolinate with the title compound-derived from Preparation 3, the above-title compound was obtained as a white solid. LC-MS, 497 (M+1). HPLC: Rt=7.12 min. Method 3 Column: SunFire C18 (150×4.6 mm) 3.5μ; Solvent A=0.05% TFA in H$_2$O: MeCN (95:5); Solvent B=0.05% TFA in H$_2$O:MeCN (5:95); 10% B to 100% B over 12 min with 3 min hold. $^1$H NMR (400 MHz, methanol-d$_3$) δ ppm 9.33 (1 H, d, J=1.8 Hz), 8.64 (1 H, dd, J=8.3, 2.2 Hz), 8.40 (2 H, s), 8.26 (1 H, d, J=8.3 Hz), 7.77 (1 H, d, J=7.5 Hz), 7.54 (1 H, d, J=7.9 Hz), 7.14-7.25 (1 H, m), 7.00 (1 H, td, J=8.1, 4.8 Hz), 6.77 (1 H, d, J=7.9 Hz), 4.69 (1 H, s), 3.95-4.08 (3 H, m), 1.42 (6 H, d, J=5.7 Hz).

Example 27

(S)-2-(5-(5-(2-(1H-Imidazo[4,5-b]pyrazin-2-yl)propan-2-yl)-9-fluoro-5H-chromeno[2,3-b]pyridin-2-yl)pyridin-2-yl)propan-2-ol

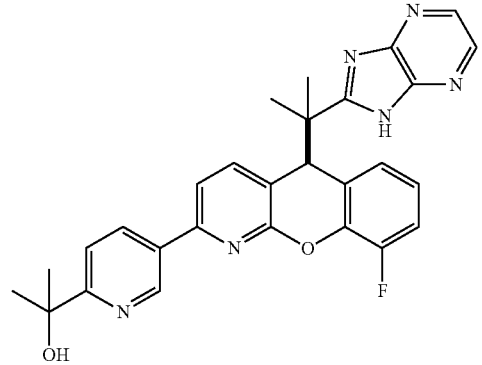 [SMILES: CC(C)(O)c1ccc(-c2ccc3c(n2)Oc2c(F)cccc2[C@@H]3C(C)(C)c2nc3nccnc3[nH]2)cn1]

To a solution of the title compound-derived from example (Example 26), (S)-methyl 5-(5-(2-(1H-imidazo[4,5-b]pyrazin-2-yl)propan-2-yl)-9-fluoro-5H-chromeno[2,3-b]pyridin-2-yl)picolinate (71 mg, 0.143 mmol), in THF, was added methylmagnesium bromide (0.715 mL, 2.145 mmol) at −10° C. The mixture was then stirred at r.t for 1.5 h. The mixture was quenched with water (2 mL) and diluted with AcOEt (50 mL), and water (20 mL). The organic layer was collected, washed with saturated NaHCO$_3$ (2×30 mL), dried over (Na$_2$SO$_4$), and concentrated under vacuo to give the crude product which was purified with a prep HPLC to provide the above title compound as a TFA salt. LC-MS, 497 (M+1). HPLC: Rt=5.64 min. Method 3 Column: SunFire C18 (150×4.6 mm) 3.5μ; Solvent A=0.05% TFA in H₂O: MeCN (95:5); Solvent B=0.05% TFA in H₂O:MeCN (5:95); 10% B to 100% B over 12 min with 3 min hold. $^1$H NMR (400 MHz, methanol-d₃) δ ppm 9.19 (1 H, d, J=1.8 Hz), 9.00 (1 H, dd, J=8.6, 2.0 Hz), 8.31 (2 H, s), 8.08 (1 H, d, J=8.8 Hz), 7.75 (1 H, d, J=7.5 Hz), 7.53 (1 H, d, J=7.5 Hz), 7.05-7.21 (1 H, m), 6.94 (1 H, td, J=8.0, 5.1 Hz), 6.71 (1 H, d, J=7.9 Hz), 4.62 (1 H, s), 1.61 (6 H, s), 1.34 (6 H, d, J=4.8 Hz).

Example 28

(S)-5-(2-(1H-Imidazo[4,5-b]pyrazin-2-yl)propan-2-yl)-9-fluoro-2-(6-fluoropyridin-3-yl)-5H-chromeno[2,3-b]pyridine

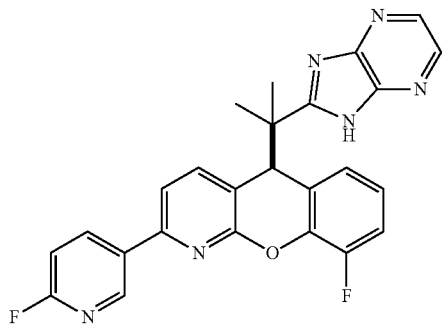 [SMILES: CC(C)(c1nc2nccnc2[nH]1)[C@@H]1c2ccc(-c3ccc(F)nc3)nc2Oc2c(F)cccc21]

Using the procedure described for Example 1 by reaction of 6-fluoropyridin-3-ylboronic acid with the title compound-derived from Preparation 3, the above-title compound was obtained as a white solid. LC-MS, 457 (M+1). HPLC: Rt=8.03 min. Method 3 Column: SunFire C18 (150×4.6 mm) 3.5μ; Solvent A=0.05% TFA in H₂O: MeCN (95:5); Solvent B=0.05% TFA in H₂O:MeCN (5:95); 10% B to 100% B over 12 min with 3 min hold. $^1$H NMR (400 MHz, DMSO-d₆) δ ppm 8.89 (1 H, d, J=2.2 Hz), 8.60 (1 H, td, J=8.3, 2.6 Hz), 8.35 (2 H, s), 7.78 (1 H, d, J=7.9 Hz), 7.42 (1 H, d, J=7.9 Hz), 7.22-7.33 (2 H, m), 6.99 (1 H, td, J=8.0, 5.1 Hz), 6.69 (1 H, d, J=7.5 Hz), 4.71 (1 H, s), 1.26 (6 H, d, J=6.2 Hz).

Example 29

(S)-5-(5-(2-(1H-Imidazo[4,5-b]pyrazin-2-yl)propan-2-yl)-9-fluoro-5H-chromeno[2,3-b]pyridin-2-yl)-N,N-dimethylpyridin-2-amine

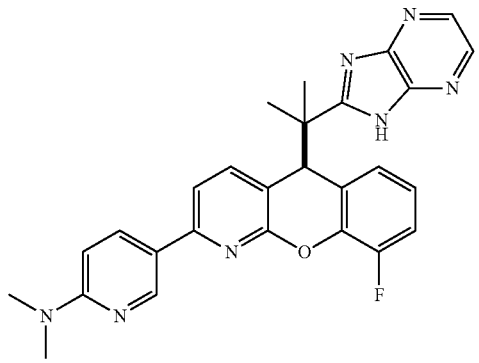 [SMILES: CN(C)c1ccc(-c2ccc3c(n2)Oc2c(F)cccc2[C@@H]3C(C)(C)c2nc3nccnc3[nH]2)cn1]

Using the procedure described for Example 1 by reaction of 6-fluoropyridin-3-ylboronic acid with the title compound-derived from Preparation 3, the above-title compound was obtained as a as TFA salt. LC-MS, 482 (M+1). HPLC: Rt=5.93 min. Method 3 Column: SunFire C18 (150×4.6 mm) 3.5μ; Solvent A=0.05% TFA in H₂O: MeCN (95:5); Solvent B=0.05% TFA in H₂O:MeCN (5:95); 10% B to 100% B over 12 min with 3 min hold. $^1$H NMR (400 MHz, methanol-d₃) δ ppm 8.54 -8.67 (2 H, m), 8.40 (2 H, s), 7.61 (1 H, d, J=7.5 Hz), 7.50 (1 H, d, J=7.9 Hz), 7.30-7.41 (1 H, m), 7.14-7.25 (1 H, m), 7.02 (1 H, td, J=8.0, 5.1 Hz), 6.79 (1 H, d, J=7.9 Hz), 4.67 (1 H, s), 3.33-3.41 (6 H, m), 1.41 (6 H, d, J=8.8 Hz).

Example 30

(S)-(5-(5-(2-(1H-Imidazo[4,5-b]pyrazin-2-yl)propan-2-yl)-9-fluoro-5H-chromeno[2,3-b]pyridin-2-yl)pyridin-2-yl)(morpholino)methanone

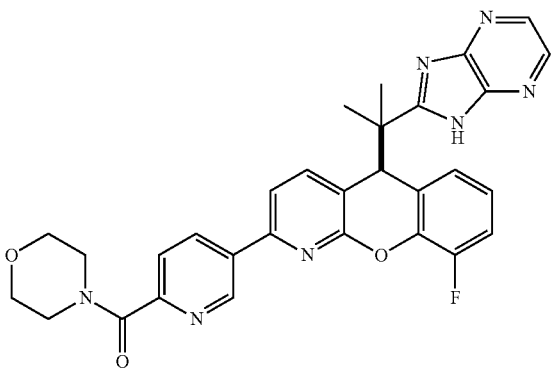 [SMILES: CC(C)(c1nc2nccnc2[nH]1)[C@@H]1c2ccc(-c3ccc(C(=O)N4CCOCC4)nc3)nc2Oc2c(F)cccc21]

Using the procedure described for Example 1 by reaction of 6-(morpholine-4-carbonyl)pyridin-3-ylboronic acid-derived from Preparation 9 and with the title compound-derived from Preparation 3, the above-title compound was obtained as a white solid. LC-MS, 552 (M+1). HPLC: Rt=3.16 min. Method 2 Column: CHROMOLITH® SpeedROD 4.6×50 mm; Solvent A=10% MeOH–90% H₂O, 0.2% H₃PO₄; Solvent B=90% MeOH–10% H₂O, 0.2% H₃PO₄; 0% B to 100% B over 4 min with 1 min hold. $^1$H NMR (400 MHz, methanol-d₃) δ ppm 9.24 (1 H, d, J=1.8 Hz), 8.57 (1 H, dd, J=8.3, 2.2 Hz), 8.40 (2H, s), 7.73 (2 H, t, J=8.1 Hz), 7.52 (1 H, d, J=7.5 Hz), 7.19 (1 H, t, J=9.4 Hz), 7.00 (1 H, td, J=7.9, 4.8 Hz), 6.76 (1 H, d, J=7.9 Hz), 4.70 (1 H, s), 3.80 (4 H, s), 3.62-3.71 (2 H, m), 3.51-3.63 (2 H, m), 1.42 (6 H, d, J=6.2 Hz).

Example 31

(S)-5-(2-(1H-Imidazo[4,5-b]pyrazin-2-yl)propan-2-yl)-9-fluoro-2-(4-(1-methyl-1H-tetrazol-5-yl)phenyl)-5H-chromeno[2,3-b]pyridine

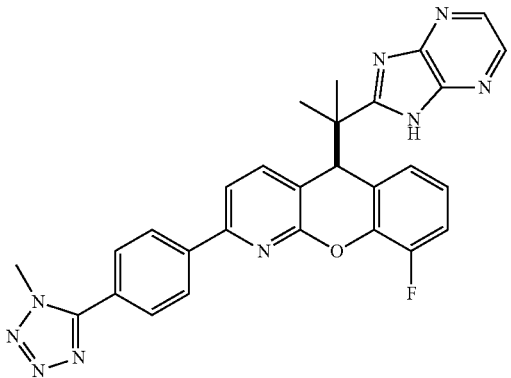 [SMILES: Cn1nnnc1-c1ccc(-c2ccc3c(n2)Oc2c(F)cccc2[C@@H]3C(C)(C)c2nc3nccnc3[nH]2)cc1]

Step 1: To a solution of (S)-2-(9-fluoro-2-(4-(1-methyl-1H-tetrazol-5-yl)phenyl)-5H-chromeno[2,3-b]pyridin-5-yl)-2-methylpropanoic acid (100 mg, 0.224 mmol)-derived from Preparation 8 in DCM (3 mL) was added 2,4,6-trifluoro-1,3,5-triazine (36.4 mg, 0.269 mmol), Pyridine (0.022 mL, 0.269 mmol), and stirred at r.t for 1 h. The reaction mixture was diluted with AcOEt (50 mL), which was then washed with saturated NaHCO$_3$ (2×20 mL), dried over Na$_2$SO$_4$, and concentrated under vacuo to give the crude compound which was used as is. LC-MS, 448 (M+1).

Step 2: To a solution of (S)-2-(9-fluoro-2-(4-(1-methyl-1H-tetrazol-5-yl)phenyl)-5H-chromeno[2,3-b]pyridin-5-yl)-2-methylpropanoyl fluoride (100 mg, 0.223 mmol), derived from the previous step, in DMF (3 mL) was added pyrazine-2,3-diamine (36.9 mg, 0.335 mmol), Pyridine (0.022 mL, 0.268 mmol), and stirred at 75° C. for o/n. The reaction mixture was diluted with AcOEt (50 mL), which was then washed with saturated NaHCO$_3$ (2×20 mL), dried over Na$_2$SO$_4$, and concentrated under vacuo to give the crude compound which was used as is. LC-MS, 538 (M+1). $^1$H NMR (400 MHz, chloroform-d) δ ppm 8.26-8.35 (2 H, m), 7.96-8.05 (2 H, m), 7.84-7.92 (2 H, m), 7.79 (1 H, d, J=7.9 Hz), 7.63-7.71 (2 H, m), 7.03-7.11 (2 H, m), 5.39 (1 H, s), 4.69 (1 H, s), 4.23 (3 H, s), 1.57 (2 H, br. s.), 1.19-1.29 (6 H, m).

Step 3: The solution of (S)-N-(3-aminopyrazin-2-yl)-2-(9-fluoro-2-(4-(1-methyl-1H-tetrazol-5-yl)phenyl)-5H-chromeno[2,3-b]pyridin-5-yl)-2-methylpropanamide (40 mg, 0.074 mmol), derived from the previous step, in AcOH (3 mL) was stirred at 90° C. for 4 h. After cooling, the solid was collected with filtration and then washed with MeOH, dried on the pump to give the above title compound. LC-MS, 520 (M+1). $^1$H NMR (400 MHz, DMSO-d$_6$) δ ppm 8.34 (4 H, d, J=8.6 Hz), 8.01 (2 H, d, J=8.6 Hz), 7.88 (1 H, d, J=7.9 Hz), 7.42-7.53 (1 H, m), 7.28-7.40 (1 H, m), 6.98-7.11 (1 H, m), 6.72-6.83 (1 H, m), 4.79 (1 H, s), 4.16-4.29 (3 H, m), 1.33 (6 H, d, J=7.9 Hz).

Biological Activity Data

The glucocorticoid receptor (GR) binding affinity (Ki) of Examples ("Ex.") 1 to 31, the accompanying AP-1 activity, and AP-1 maximum inhibition values are given in the table below. The data presented below were obtained using the assays referred to in the table and described herein in the ASSAY section supra.

| Ex. No. | GR ($K_i$, nM) (measured in GR binding Assay II) | AP-1 ($EC_{50}$, nM) (measured in cellular transrepression assay) | AP-1 Max % inhibition (measured in cellular transrepression assay) |
|---|---|---|---|
| 1 | 57.05 | 8.33 | 65.16 |
| 2 | 3.28 | 4.39 | 59.74 |
| 3 | 2.35 | 3.85 | 65.04 |
| 4 | 2.63 | 4.94 | 73.10 |
| 5 | 2.89 | 29.53 | 55.76 |
| 6 | 2.34 | 15.54 | 58.25 |
| 7 | 1.40 | 12.20 | 54.19 |
| 8 | 0.76 | 9.82 | 69.82 |
| 9 | 2.10 | 291.10 | 43.74 |
| 10 | 0.67 | 20.08 | 70.19 |
| 11 | 0.82 | 37.52 | 76.26 |
| 12 | 0.66 | 14.41 | 62.62 |
| 13 | 2.36 | 55.10 | 55.50 |
| 14 | 16.15 | 284.50 | 31.64 |
| 15 | 121.10 | 864.20 | 29.26 |
| 16 | 12.40 | 169.20 | 52.19 |
| 17 | 65.78 | 2500.00 | 27.28 |
| 18 | 15.99 | 61.12 | 50.61 |
| 19 | 70.46 | 1947.00 | 44.63 |
| 20 | 1.40 | 14.25 | 39.97 |
| 21 | 3.92 | 21.05 | 45.93 |
| 22 | 2.91 | 19.94 | 51.02 |
| 23 | 1.76 | 22.75 | 58.22 |
| 24 | 1.90 | 37.28 | 69.36 |
| 25 | 2.78 | 31.74 | 57.82 |
| 26 | 144.20 | 5000.00 | 14.32 |
| 27 | 9.30 | 28.37 | 53.63 |
| 28 | 28.65 | 5000.00 | 16.36 |
| 29 | 5.43 | 129.40 | 44.92 |
| 30 | 30.28 | 178.80 | 57.05 |
| 31 | 1.94 | 15.00 | 48.56 |

What is claimed is:
1. A compound of formula II,

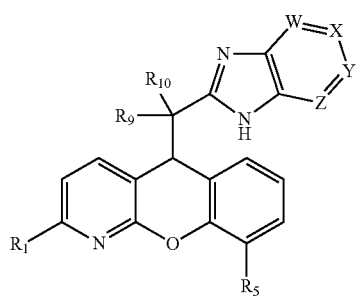

or an enantiomer, diastereomer, tautomer, or a pharmaceutically-acceptable salt thereof, wherein:

W, X, Y and Z are independently selected from N and CH;

$R_1$ is selected from 5- to 10-membered aryl and 5- to 10-membered heteroaryl, wherein said aryl and heteroaryl group are each substituted with zero to three substituents independently selected from halogen, $C_{1-6}$hydroxyalkyl, —$OR_{12}$, —$NR_{12}R_{13}$, —C(=O)$R_{12}$, —C(=O)O$R_{12}$, —C(=O)N$R_{12}R_{13}$, —$NR_{12}$C(=O)$R_{13}$, —S(O)$_2R_{14}$, —$NR_{12}$SO$_2R_{14}$, and 5- to 6-membered heteroaryl substituted with $C_{1-3}$alkyl group $R_5$ is halogen;

$R_9$ and $R_{10}$ are the same or different and at each occurrence are independently $C_{1-3}$alkyl;

$R_{12}$ and $R_{13}$ are the same or different and at each occurrence are independently selected from (i) hydrogen, $C_{1-6}$alkyl, $C_{1-6}$haloalkyl, and 5- to 6-membered heterocyclo; or (ii) where possible, $R_{12}$ is taken together with $R_{13}$ to form a 5- to 6-membered heterocyclo ring; and $R_{14}$ at each occurrence is independently $C_{1-6}$alkyl.

2. A compound as defined in claim 1, or an enantiomer, diastereomer, tautomer, or a pharmaceutically-acceptable salt thereof, wherein:
$R_1$ is phenyl or pyridyl, each of which is substituted with zero to three substituents independently selected from halogen,
$C_{1-6}$hydroxyalkyl, $-OR_{12}$, $-NR_{12}R_{13}$, $-C(=O)R_{12}$, $-C(=O)OR_{12}$, $-C(=O)NR_{12}R_{13}$, $-NR_{12}C(=O)R_{13}$, $-S(O)_2R_{14}$, $-NR_{12}SO_2R_{14}$, and 5- to 6-membered heteroaryl substituted with $C_{1-3}$alkyl group.

3. The compound as defined in claim 2, or an enantiomer, diastereomer, tautomer, or a pharmaceutically-acceptable salt thereof, wherein:
$R_1$ is phenyl or pyridyl, each of which is substituted with zero to three substituents independently selected from F, Cl, $-OCF_3$, $-NH_2$,

[chemical structures]

4. The compound as defined in claim 3, or an enantiomer, diastereomer, tautomer, or a pharmaceutically-acceptable salt thereof, wherein:
W is N;
X is CH;
Y is CH; and
Z is N.

5. The compound as defined in claim 3, or an enantiomer, diastereomer, tautomer, or a pharmaceutically-acceptable salt thereof, wherein:
W is CH;
X is CH;
Y is CH; and
Z is CH.

6. The compound as defined in claim 3, or an enantiomer, diastereomer, tautomer, or a pharmaceutically-acceptable salt thereof, wherein:
W is CH;
X is CH;
Y is CH; and
Z is N.

7. The compound as defined in claim 3, or an enantiomer, diastereomer, tautomer, or a pharmaceutically-acceptable salt thereof, wherein:
W is CH;
X is N;
Y is CH; and
Z is N.

8. The compound as defined in claim 2, wherein:
$R_1$ is

[chemical structures]

$R^a$ is H, $-OCF_3$, $-NH_2$,

[chemical structures]

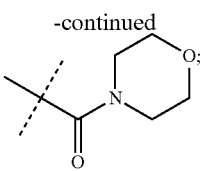

$R^b$ is H, F, or Cl; and
$R^c$ is H, F,

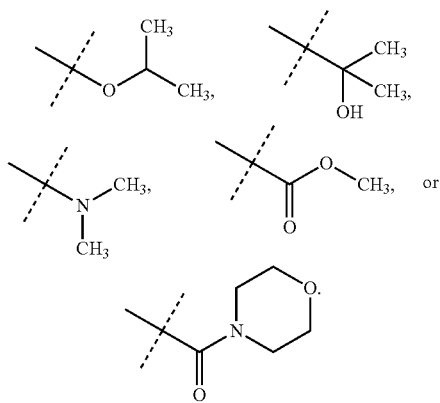

9. The compound as defined in claim 1, or an enantiomer, diastereomer, tautomer, or a pharmaceutically-acceptable salt thereof, wherein said compound is selected from: (S)-(4-(5-(2-(1H-imidazo[4,5-b]pyrazin-2-yl)propan-2-yl)-9-fluoro-5H-chromeno[2,3-b]pyridin-2-yl)phenyl)(morpholino)methanone (1); (S)-1-(4-(5-(2-(1H-imidazo[4,5-b]pyrazin-2-yl)propan-2-yl)-9-fluoro-5H-chromeno[2,3-b]pyridin-2-yl)phenyl)ethanone (2); (S)-2-(4-(5-(2-(1H-imidazo[4,5-b]pyrazin-2-yl)propan-2-yl)-9-fluoro-5H-chromeno[2,3-b]pyridin-2-yl)phenyl)propan-2-ol (3); (S)-4-(5-(2-(1H-imidazo[4,5-b]pyrazin-2-yl)propan-2-yl)-9-fluoro-5H-chromeno[2,3-b]pyridin-2-yl)-N,N-dimethylbenzamide (4); (S)-5-(2-(1H-imidazo[4,5-b]pyrazin-2-yl)propan-2-yl)-9-fluoro-2-(4-(methylsulfonyl)phenyl)-5H-chromeno[2,3-b]pyridine (5); (S)-5-(2-(1H-imidazo[4,5-b]pyrazin-2-yl)propan-2-yl)-2-(4-(ethylsulfonyl)phenyl)-9-fluoro-5H-chromeno[2,3-b]pyridine (6); (S)-5-(2-(1H-imidazo[4,5-b]pyrazin-2-yl)propan-2-yl)-9-fluoro-2-(4-(isopropylsulfonyl)phenyl)-5H-chromeno[2,3-b]pyridine (7); (S)-5-(2-(1H-imidazo[4,5-b]pyrazin-2-yl)propan-2-yl)-9-fluoro-2-(4-isopropoxyphenyl)-5H-chromeno[2,3-b]pyridine (8); (S)-5-(2-(1H-imidazo[4,5-b]pyrazin-2-yl)propan-2-yl)-2-(3-chloro-4-isopropoxyphenyl)-9-fluoro-5H-chromeno[2,3-b]pyridine (9); (S)-5-(2-(1H-imidazo[4,5-b]pyrazin-2-yl)propan-2-yl)-9-fluoro-2-(3-fluoro-4-isopropoxyphenyl)-5H-chromeno[2,3-b]pyridine (10); (S)-5-(2-(1H-imidazo[4,5-b]pyrazin-2-yl)propan-2-yl)-2-(4-tert-butoxyphenyl)-9-fluoro-5H-chromeno[2,3-b]pyridine (11); (S)-5-(2-(1H-imidazo[4,5-b]pyrazin-2-yl)propan-2-yl)-2-(4-ethoxyphenyl)-9-fluoro-5H-chromeno[2,3-b]pyridine (12); (S)-5-(2-(1H-imidazo[4,5-b]pyrazin-2-yl)propan-2-yl)-9-fluoro-2-(4-(trifluoromethoxy)phenyl)-5H-chromeno[2,3-b]pyridine (13); (S)-(4-(5-(2-(1H-benzo[d]imidazol-2-yl)propan-2-yl)-9-fluoro-5H-chromeno[2,3-b]pyridin-2-yl)phenyl)(morpholino)methanone (14); (S)-(4-(5-(2-(3H-imidazo[4,5-b]pyridin-2-yl)propan-2-yl)-9-fluoro-5H-chromeno[2,3-b]pyridin-2-yl)phenyl)(morpholino)methanone (15); (S)-(4-(5-(2-(9H-purin-8-yl)propan-2-yl)-9-fluoro-5H-chromeno[2,3-b]pyridin-2-yl)phenyl)(morpholino)methanone (16); (S)-5-(2-(9H-purin-8-yl)propan-2-yl)-9-fluoro-2-(4-(methylsulfonyl)phenyl)-5H-chromeno[2,3-b]pyridine (17); (S)-5-(2-(1H-imidazo[4,5-b]pyrazin-2-yl)propan-2-yl)-9-fluoro-2-(4-morpholinophenyl)-5H-chromeno[2,3-b]pyridine (18); (S)-N-(4-(5-(2-(1H-imidazo[4,5-b]pyrazin-2-yl)propan-2-yl)-9-fluoro-5H-chromeno[2,3-b]pyridin-2-yl)phenyl)acetamide (19); (S)-5-(2-(1H-imidazo[4,5-b]pyrazin-2-yl)propan-2-yl)-9-fluoro-2-phenyl-5H-chromeno[2,3-b]pyridine (20); (S)-5-(2-(1H-imidazo[4,5-b]pyrazin-2-yl)propan-2-yl)-9-fluoro-2-(pyridin-4-yl)-5H-chromeno[2,3-b]pyridine (21); (S)-4-(5-(2-(1H-imidazo[4,5-b]pyrazin-2-yl)propan-2-yl)-9-fluoro-5H-chromeno[2,3-b]pyridin-2-yl)aniline (22); (S)-N-(4-(5-(2-(1H-imidazo[4,5-b]pyrazin-2-yl)propan-2-yl)-9-fluoro-5H-chromeno[2,3-b]pyridin-2-yl)phenyl)methanesulfonamide (23); (S)-1-(4-(5-(2-(1H-imidazo[4,5-b]pyrazin-2-yl)propan-2-yl)-9-fluoro-5H-chromeno[2,3-b]pyridin-2-yl)phenyl)pyrrolidin-2-one (24); (S)-5-(2-(1H-imidazo[4,5-b]pyrazin-2-yl)propan-2-yl)-9-fluoro-2-(6-isopropoxypyridin-3-yl)-5H-chromeno[2,3-b]pyridine (25); (S)-methyl 5-(5-(2-(1H-imidazo[4,5-b]pyrazin-2-yl)propan-2-yl)-9-fluoro-5H-chromeno[2,3-b]pyridin-2-yl)picolinate (26); S)-2-(5-(5-(2-(1H-imidazo[4,5-b]pyrazin-2-yl)propan-2-yl)-9-fluoro-5H-chromeno[2,3-b]pyridin-2-yl)pyridin-2-yl)propan-2-ol (27); (S)-5-(2-(1H-imidazo[4,5-b]pyrazin-2-yl)propan-2-yl)-9-fluoro-2-(6-fluoropyridin-3-yl)-5H-chromeno[2,3-b]pyridine (28); (S)-5-(5-(2-(1H-imidazo[4,5-b]pyrazin-2-yl)propan-2-yl)-9-fluoro-5H-chromeno[2,3-b]pyridin-2-yl)-N,N-dimethylpyridin-2-amine (29); (S)-(5-(5-(2-(1H-imidazo[4,5-b]pyrazin-2-yl)propan-2-yl)-9-fluoro-5H-chromeno[2,3-b]pyridin-2-yl)pyridin-2-yl)(morpholino)methanone (30); and (S)-5-(2-(1H-imidazo[4,5-b]pyrazin-2-yl)propan-2-yl)-9-fluoro-2-(4-(1-methyl-1H-tetrazol-5-yl)phenyl)-5H-chromeno[2,3-b]pyridine (31).

10. A pharmaceutical composition comprising a compound as defined in claim 1 and a pharmaceutically acceptable carrier therefor.

* * * * *